US006805880B1

(12) United States Patent
Højgaard et al.

(10) Patent No.: US 6,805,880 B1
(45) Date of Patent: Oct. 19, 2004

(54) PHARMACEUTICAL DELIVERY SYSTEM FOR VITAMIN C AND VITAMIN E AND USE OF A COMBINATION OF VITAMIN C AND E FOR PREVENTING OR TREATING CONDITIONS INVOLVING OXIDATIVE STRESS

(75) Inventors: Bent Højgaard, Allerød (DK); Henrik Enghusen Poulsen, Humlebæk (DK); Jukka Salonen, Jännevirta (FI)

(73) Assignee: Ferrosan A/S, Soborg (DK)

(*) Notice: Subject to any disclaimer, the term of this patent is extended or adjusted under 35 U.S.C. 154(b) by 0 days.

(21) Appl. No.: 09/642,160

(22) Filed: Aug. 21, 2000

Related U.S. Application Data

(60) Provisional application No. 60/149,726, filed on Aug. 20, 1999.

(30) Foreign Application Priority Data

Aug. 20, 1999 (DK) .......................................... 1999 01145

(51) Int. Cl.[7] .............................. A61K 9/22; A61K 9/24
(52) U.S. Cl. ....................... 424/468; 424/472; 424/458; 424/457
(58) Field of Search ................................ 424/468, 457, 424/472, 474, 458; 514/458, 474

(56) References Cited

U.S. PATENT DOCUMENTS

| 5,560,928 A | * | 10/1996 | DeFilce ...................... 424/466 |
| 5,871,766 A | * | 2/1999 | Hennekens .................. 424/422 |
| 5,972,985 A | * | 10/1999 | Thomas et al. ............. 514/400 |
| 6,054,128 A | * | 4/2000 | Wakat ......................... 424/765 |
| 6,136,859 A | * | 10/2000 | Henriksen ................... 514/561 |

FOREIGN PATENT DOCUMENTS

EP 820 703 * 1/1998

OTHER PUBLICATIONS

Sato et al Synergism of tocopherol and ascorbate on the survival of cultured brain neurones Neuropharm and Neurotox 4:1179–1182 1993.*

Niki Interaction of ascorbate and alpha–tocopherol Annals New York Academy of Sciences 186–199 1986.*

Porkkala, Elina K., et al: "A randomized, single–blind, placebo–controlled trial of the effects of 200 mg α–tocopherl on the oxidation resistance of atherongenic lipoproteins", *Am. J. Clin. Nutr.*, vol. 68, pp. 1034–1041, 1998.

Ginter, E., et al: "Synergism Between Vitamins C and E: Effect on Microsomal Hydroxylation on Guinea Pig Liver", *Intern. J. Vit. Nutr. Res.* 52, pp. 55–59, 1982.

Berry, Eliot M., et al: "Synergism between vitamins E and C: biological implications for future research", *Int. J. Cancer*, vol. 83, p. 288, 1999.

Baker, Herman, et al: Human Plasma Patterns During 14 Days Ingestion of Vitamin E, Beta–Carotene, Ascorbic Acid, and Their Various Combinations, *Journal of the American College of Nutrition*, vol. 15, No. 2, pp. 159–163, 1996.

Cadenas, Susana et al: "Phospholipid Hydroperoxides and Lipid Peroxidation in Liver and Plasma of ODS Rats Supplemented with α–Tocopherol and Ascorbic Acid", *Free Rad. Res.*, vol. 26, No. 4, pp. 485–493, 1996.

(List continued on next page.)

*Primary Examiner*—James M. Spear
(74) *Attorney, Agent, or Firm*—Finnegan, Henderson, Farabow, Garrett & Dunner, L.L.P.

(57) ABSTRACT

A pharmaceutical delivery system comprising a slow-release formulation of vitamin C (ascorbic acid) and a plain-release formulation of vitamin E (tocopherol) has been found to raise and maintain the concentrations of these vitamins in the blood plasma to a ratio of approximately 2.2:1. The steady-state concentration and ratio of these antioxidants has been found to be critical in the prevention and treatment of oxidative stress related disorders such as arteriosclerosis and diabetes and neural degenerative disorders such as Alzheimer's Disease.

15 Claims, 3 Drawing Sheets

OTHER PUBLICATIONS

Niki, Etsuo, et al: "Interaction among vitamin C, vitamin E, and β–carotene", *Am. J. Clin. Nutr.*, vol. 62, pp. 1322S–1326S, 1995.

Brude, Ingeborg R., et al: "Peroxidation of LDL From Combined—Hyperlipidemic Male Smokers Supplied With ω–3 Fatty Acids and Antioxidants", *Arteriosclerosis, Thrombosis, and Vascular Biology*, vol. 17, No. 11, pp. 2576–2588, 1997.

Shklar, Gerald, et al: "The Effectiveness of a Mixture of β–Carotene, α–Tocopherol, Glutathione, and Ascorbic Acid for Cancer Prevention", *Nutrition and Cancer*, vol. 20, No. 2, pp. 145–151, 1993.

Sato, Kaoru, et al: "Synergism of tocopherol and ascorbate on the survival of cultured brain neurones", *Neuro Report*, 4, pp. 1179–1182, 1993.

Igarashi, Osamu, et al: "Synergistic Action of Vitamin E and Vitamin C in vivo Using a New Mutant of Wistar–Strain Rats, ODS, Unable to Synthesize Vitamin C", *J. Nutr. Sci. Vitaminol*, 37, pp. 359–369, 1991.

van den Berg, Jeroen J.M., et al: "The cooperative action of vitamins E and C in the protection against peroxidation of parinaric acid in human erythrocyte membranes", *Chemistry and Physics of Lipids*, vol. 53, pp. 309–320, 1990.

Nègre–Salvayre, Anne, et al: "α–Tocopherol, Ascorbic Acid, and Rutin Inhibit Synergistically the Copper–Promoted LDL Oxidation and the Cytotoxicity of Oxidized LDL to Cultured Endothelial Cells", *Biological Trace Element Research*, vol. 47, pp. 81–89, 1995.

Thomas, Craig, E., et al: "Ascorbate and Phenolic Antioxidant Interactions in Prevention of Liposomal Oxidation", *Lipids*, vol. 27, No. 7, pp. 543–549, 1992.

Strain, J. J., et al: "Vitamin C and vitamin E—synergistic interactions in vivo?", *Free Radicals and Aging*, pp. 419–422, 1992.

Niki, Etsuo: "Interaction of Ascorbate and α–Tocopherol", *Annals New York Academy of Sciences*, pp. 186–199, 1986.

Nègre–Salvayre, A., et al: "Additional Antilipoperoxidant Activities of Alpha–Tocopherol and Ascorbic Acid on Membrane–like Systems are Potentiated by Rutin", *Pharmacology*, vol. 42, pp. 262–272, 1991.

Bassenge, Eberhard et al: "Tolerance to nitrates and simultaneous upregulation of platelet activity prevented by enhancing antioxidant state", *Naunyn–Schmiedeberg's Arch Pharmacol*, vol. 353, pp. 363–367, 1996.

Bruun–Jensen, Lone et al: "Antioxidant synergism between tocopherols and ascorbyl palmitate in cooked, minced turkey", *Z Lebensm Unters Forsch*, vol. 199, pp. 210–213, 1994.

Darr, Douglas et al: "Effectiveness of Antioxidants (Vitamin C and E) With and Without Sunscreens as Topical Photoprotectants", *Acta Derm Venereol*, vol. 76, pp. 264–268, 1996.

Sato, Keizo et al: "Free Radical–Mediated Chain Oxidation of Low Density Lipoprotein and Its Synergistic Inhibition by Vitamin E and Vitamin C", *Archives of Biochemistry and Biophysics*, vol. 279. No. 2, pp. 402–405, 1990.

Böhm, F. et al: "β–Carotene with vitamins E and C offers synergistic cell protection against $NO_x$", *FEBS Letters 436*, pp. 387–389, 1998.

Lambelet, P., et al: "Chemical evidence for interactions between vitamins E and C", *Experientia*, vol. 41, 1985, pp. 1384–1388.

May, James M., et al: "Vitamin C recycling and function in human monocytic U–937 cells", *Free Radical Biology & Medicine*, vol. 26, Nos. 11/12, pp. 1513–1523, 1999.

Gaziano, Michael J: "Antioxidant Vitamins and Cardiovascular Disease", *Proceedings of the Association of American Physicians*, vol. 111, No. 1, pp. 2–9, 1999.

Tribble, Diane L: "Antioxidant Consumption and Risk of Coronary Heart Disease: Emphasis on Vitamin C, Vitamin E, and β–Carotene", *AHA Science Advisory*, Circulation, vol. 99, pp. 591–595, 1999.

McAuliffe, Aileen V., et al: "Administration of Ascorbic Acid and an Aldose Reductase Inhibitor (Tolrestat) in Diabetets: Effect on Urinay Albumin Excretion", *Nephron*, vol. 80, pp. 277–284, 1998.

Nyyssönen, K., et al: "Effect of supplementation of smoking men with plain or slow release ascorbic acid on lipoprotein oxidation", *European Journal of Clinical Nutrition*, vol. 51, pp. 154–163, 1997.

Fuller, Cindy J, et al: "RRR–α–tocopheryl acetate supplementation at pharmacologic doses decreases low–density–lipoprotein oxidative susceptibility but not protein glycation in patients with diabetes mellitus", *American Journal for Clinical Nutrition*, vol. 63, pp. 753–759, 1996.

Jialal, Ishwarlal and Sridevi Devaraj: "Low–density lipoprotein oxidation, antioxidants, and atherosclerosis: a clinical biochemistry perspective", *Clinical Chemistry*, vol. 42, No. 4, 498–506, 1996.

Rouhianinen, Päivi et al: "Association between Low Plasma Vitamin E Concentration and Progression of Early Cortical Lens Opacities", *American Journal of Epidemiology*, vol. 144, No. 5, pp. 496–500, 1996.

Bowry, Vincent W, et al: "Prevention of Tocopherol–mediated Peroxidation in Ubiquinol–10–free Human Low Density Lipoprotein", *Journal of Biological Chemistry*, vol. 270, No. 11, pp. 5756–5763, 1995.

De Mulder, Cathérine L.C., et al: "Protection by vitamin E, selenium, trolox, ascorbic acid palmitate, acetylcysteine, coenzyme Q, β–carotene, and (+)–catechin against oxidative damage to rat liver and heart tissue slices measured by oxidized heme proteins", *J. Nutr. Bio chem.*, vol. 6, pp. 452–458, 1995.

Thomas, Shane R., et al: "Coantioxidants make α–tocopherol an efficient antioxidant for low–density lipoprotein", *American J. Clin. Nutr.* vol. 62, pp. 1357S–1364S, 1995.

Sies, Helmut and Wilhelm Stahl: "Vitamins E and C, β–carotene, and other carotenoids as antioxidants", *American J. Clin. Nutr.*, vol. 62, pp. 1315S–1321S, 1995.

Niki, Etsuo, et al.: "Interaction among vitamin C, vitamin E, and β–carotene", *American J. Clin. Nutr.*, vol. 62, pp. 1322S–1326S, 1995.

Hennekens, Charles H., et al: "Antioxidant vitamin–cardiovascular disease hypothsis is still promising, but still unproven: the need for randomized trials", *American J. Clin. Nutr.*, vol. 62, pp. 1377S–1380S, 1995.

Jialal, Ishwarlal, et al: "The Effect of α–Tocopherol Supplementation on LDL Oxidation", *Arteriosclerosis, Thrombosis, and Vascular Biology*, vol. 15, No. 2, Feb. 1995, pp. 190–198.

Bowen, P.E., et al: "β–Carotene, Vitamin E, Vitamin C and Quercetin in the Prevention of Degenerative Disease", Summary of workshop held in Jun. 1994, ILSI Europe—Antioxidant Task Force, pp. 2–16, 1994.

Tribble, Diane L., et al: "Oxidative suseptibility of low density lipoprotein subfractions is related to their ubiquinol–10 and α–tocopherol content", *Proc. Natl. Acad. Sci.,* vol. 91, pp. 1183–1187, 1994.

Halliwell, Barry: "Free Radicals, antioxidants, and human disease: curiosity, cause, or consequence?", *The Lancet,* vol. 344, pp. 721–724, 1994.

Heinecke, Jay W: "Cellular mechanisms for the oxidative modification of lipoproteins: implications for atherogenesis", *Coronary Artery Disease,* vol. 5, pp. 205–210, 1994.

Meydani, Mohsen: "Vitamin E", *The Lancet,* vol. 345, 170–175, 1995.

Ingold, Keith U., et al: "Autoxidation of lipids and antioxdation by α–tocopherol and ubiquinol in homogeneous solution and in aqueous dispersions of lipids: Unrecognized consequences of lipid particle size as exemplified by oxidation of human low density lipoprotein", *Proc. Natl. Acad. Sci.,* vol. 90, pp. 45–49, 1993.

Jialal, I., et al: "Effect of combined Supplementation With α–Tocopherol, Ascorbate, and Beta Carotene on Low–Density Lipoprotein Oxidation" *Circulation,* vol. 88, No. 6, pp. 2780–2786, 1993.

Witztum, Joseph L.: "The Oxidation Hypothesis of Atherosclerosis", *The Lancet,* vol. 344, pp. 793–795, 1994.

Grisham, Mathew B., "Oxidants and Free Radicals in Inflammatory Bowel Disease", *The Lancet,* vol. 344, pp. 859–861, 1994.

Cerutti, Peter A., "Oxy–Radicals and Cancer", *The Lancet,* vol. 344, pp. 862–863, 1994.

Cross, Carroll E. et al., "Reactive Oxygen Species and the Lung", *The Lancet,* vol. 344, pp. 930–933, 1994.

Slyper, Arnold H., "A Fresh Look at the Atherogenic Remnant Hypothesis", *The Lancet,* vol. 340, pp. 289–291, 1992.

Esterbauer, Hermann et al., "The Role of Lipid Peroxidation and Antioxidants in Oxidative Modification LDL", *Free Radical Biology & Medicine,* vol. 13, pp. 341–390, 1992.

Jialal, I. et al., "Influence of Antioxidant Vitamins on LDL Oxidation", *Annals NY Academy of Sciences,* vol. 669, pp. 237–247, 1992.

Jialal, I. et al., "Effect of Dietary Supplementation with Alphatocopherol on the Oxidative Modification of Low Density Lipoprotein", *Journal of Lipid Research,* vol. 33, pp. 899–906, 1992.

Kagan, Valerian E. et al., "Recycling of Vitamin E in Human Lowe Density Lipoproteins", *Journal of Lipid Research,* vol. 33, pp. 385–397, 1992.

Stocker, Roland et al., "Ubiquinol–10 Protects Human Low Density Lipoprotein More Efficiently Against Lipid Peroxidation that does α–Tocopherol", *Proc. Natl. Acad. Sci. U.S.A.,* vol. 88, pp. 1646–1650, 1991.

Esterbauer, Herman et al., "Role of Vitamin E in Preventing the Oxidation of Low–Density Lipoprotein", Am. J. Clin. Nutr., vol. 53, pp. 314S–321S, 1991.

Veris, Research Summary, "An Overview of Vitamin e Efficacy", pp. 1–36, Nov. 1998.

Veris, Research Summary, "An Overview of Vitamin e Efficacy", pp. 1–24, Jan. 1993.

Veris, Research Summary, "An Overview of Vitamin e Efficacy", pp. 1–6, Feb. 1992.

* cited by examiner

Comparative Dissolution

| diss. time | % dissolution of Vitamin E | |
|---|---|---|
| Time (min) | Tablet of Invention | Tablet Swiss One |
| 5 | 55,9 | 0 |
| 10 | 93,1 | 0 |
| 15 | 99,85 | 2,53 |
| 30 | 96,05 | 13,18 |
| 60 | 102,45 | 68,3 |

PHARMACEUTICAL DELIVERY SYSTEM FOR VITAMIN C AND VITAMIN E AND USE OF A COMBINATION OF VITAMIN C AND E FOR PREVENTING OR TREATING CONDITIONS INVOLVING OXIDATIVE STRESS

This application claims the benefit of provisional application No. 60/149,726 filed on Aug. 20, 1999.

FILED OF INVENTION

This invention relates to a pharmaceutical delivery system for obtaining a controlled ratio of antioxidants. It further relates to a principle of antioxidant levels in blood plasma.

The present invention proposes a pharmaceutical delivery system for oral delivery of the antioxidants vitamin C and vitamin E to obtain high concentrations thereof and a controlled ratio between the vitamins in blood plasma in humans and animals.

It is an object of the present invention to provide a method for the prevention or treatment of arteriosclerosis or other diseases or conditions where reactive oxygen species are involved using a delivery system for obtaining a controlled ratio of antioxidants in blood plasma.

GENERAL BACKGROUND

Free radical reactions appear in the cells of all mammalian bodies. Free radical derivatives of oxygen are of particular importance because of the use of oxygen to generate energy in the body. In the cellular processes, oxygen is reduced to water through the addition of 4 electrons, a process that is tightly controlled (1). Reactive oxygen species (ROS) are intermediary products produced during this process. These include superoxide anions, hydrogen peroxide, and hydroxyl radicals. The ROS are highly reactive and modify important cellular macromolecules (2). ROS initiate or accelerate disease processes.

The formation of ROS can occur as part of many cellular processes including mitochondrial respiration, immune cell responses, cell injury, heat, radiation of many origins, from metabolism of drugs and other chemicals. ROS are thought to be involved in almost all disease processes and the ageing process. For example, modification can occur to lipids in the LDL (light density lipoprotein) particle in the blood (3). This modification leads to increased formation of fatty streaks in the arterial wall and subsequent formation of arterisclerotic plaques (3b, 4) which can compromise blood supply to organs, causing manifest disease, e.g. coronary heart attack.

The body and its cells have several mechanisms to control the effects of ROS. The general term of such mechanisms is antioxidants. Antioxidants include enzymes, substances produced in the body and substances that are only found in food. Examples of the latter are antioxidant vitamins (E, C, A) and similar substances (flavonoids, lycopene, beta-carotene). The substances have different properties, some being water-soluble others being fat-soluble (2).

During the last decades, evidence has gathered linking both high intake of food rich in antioxidants, and intake of supplements containing antioxidant vitamins to reduce incidence of cancer and arteriosclerosis (5).

A particularly important part of the lipid phase is the LDL particle (low density lipoproteins). These particles are produced in the liver and are responsible for transport of lipids, particularly cholesterol. These particles are taken up by cells by a protein moiety APO-B100, an uptake which is feedback inhibited. If LDL is oxidised, it cannot be taken up, but is then devoured by monocyte derived macrophages with no feed-back inhibition. Macrophages can transform into foam cells when large amounts of LDL are taken up. The foam cells deposit in the arterial wall and contribute to the development of arteriosclerotic plaques (4).

Water-soluble antioxidants are taken up quickly, but are also eliminated quickly from the body by urinary excretion (6). Fat-soluble antioxidants are taken up more slowly and eliminated slowly from the body (7). This means that the concentration ratio of e.g. a water-soluble and a fat-soluble antioxidant vitamin will vary after intake.

Water-soluble and fat-soluble antioxidants are found, respectively, in the water phase and in the lipid phase of the body. In the transition phase between the lipid and water phases there is co-operation between the water and the fat-soluble antioxidants. An example of this is the interaction between vitamin C and vitamin E in the transition between the LDL particle and the water phase of the blood (8, 9). Vitamin E is the most important antioxidant in the LDL particle.

When vitamin E is oxidized in the LDL particle, a tocopheryl radical is generated. This radical can elicit lipid peroxidation or protein oxidation and can thus result in the oxidation of the LDL particle with the consequences described above (8). Vitamin C, ascorbic acid (AA), can prevent this process by interacting with the tocopheryl radical. This results in reduction of the tocopheryl radical to tocopherol and the formation of oxidised vitamin C, dehydro-ascorbic acid, DHAA (10). DHAA is taken up by the liver and reduced to vitamin C (11).

U.S. Pat. No. 5,897,879 discloses a sustained-release pharmaceutical delivery system for the administration of an antioxidant drug to a patient in need of such drug, wherein the said delivery system comprises the said drug in combination with a matrix, the said matrix comprising a polymer selected from the group consisting of a polymer which does not interact with the said drug and a mixture of such polymers, and the said polymeric matrix is present in amounts from about 20% (w/w) to about 80% (w/w). The drug can inter alia be vitamin E, vitamin C or a combination thereof. In the case of combination both drug components have a sustained-release form, and they are released together. This known system does not give effective high, constant concentrations of vitamin C and E.

WO 97/00672 discloses an effervescent composition comprising at least one active ingredient selected from the group consisting of a nutritional supplement, a dietary supplement and combinations thereof in amounts sufficient to provide a dosage form of the said active ingredient as few as once in a 24hour period, the said active ingredients being both a free form component and a microencapsulated component which has sustained-release properties, and an effective amount of an effervescent agent. The active agent is selected from the group consisting of camitine, calcium, magnesium, ascorbic acid, vitamin E and combinations thereof. The active agents are micro-encapsulated together. This known composition provides immediate and sustained release of both vitamin C and vitamin E. The vitamins are released together from the same delivery principle(s), and they do not provide a high, constant vitamin concentration, in the preferred ratio in the blood plasma.

EP 176772 discloses a process for increasing the delayed-release activity of vitamin C and vitamin E by incorporating both vitamins in a neutral oil and encapsulating the oil. Both vitamins are present in the same delivery principal.

EP 0820703 discloses compositions for nutritional integration comprising hydrosoluble vitamins and liposoluble vitamins, characterised in that the hydrosoluble vitamins have a prolonged-release formulation and the liposoluble vitamins have a rapid-release formulation.

A large controlled trial over more than 5 years showed no effect of a 50-mg tocopherol dose (12).

A controlled release formulation of vitamin C and E failed to give the expected increase in vitamin E plasma concentrations whereas it produced a more constant and thus favourable vitamin C concentration (13).

A study designed to test the effect of ascorbic acid, selenium, α-tocopherol and β-carotene on the oxidation resistance of VLDL and LDL (14) demonstrated that the oxidation resistance of atherogenic lipoproteins in human plasma required the combined elevated levels of selenium and antioxidative vitamins or elevated doses of β-carotene and α-tocopherol.

The present invention solves the problem of providing high concentrations of vitamin C and E in the preferred ratio by using a pharmaceutical delivery system for oral delivery of vitamin C and vitamin E to obtain high concentrations thereof in a controlled ratio in blood plasma in humans or animals by a delivery system with slow release of vitamin C and plain release of vitamin E.

The present invention seeks to provide a method of providing oxidation resistance without the use of selenium or β-carotene by providing high concentrations of vitamin C and E at a controlled ratio in blood plasma.

SUMMARY OF THE INVENTION

The present invention relates to a pharmaceutical delivery system for oral delivery of the antioxidants vitamin C and vitamin E to obtain high concentrations thereof and a controlled ratio between vitamin C and vitamin E in blood plasma in humans or animals, characterised in that it has a slow release formulation of vitamin C and a plain release formulation of vitamin E.

The invention relates to a method of treating or preventing oxidative stress disorders and associate diseases comprising the administration to an individual a combination of vitamin C and vitamin E in sufficient amounts so as to raise, within 8 weeks of the first administration, the concentration of said vitamins in blood plasma sufficiently and to a ratio of from 1:1 to 3:1, preferably 2.2:1.

The invention further relates to a method of treating or preventing oxidative stress disorders and associate diseases comprising the daily administration to an individual at least one dosage unit comprising a combination of vitamin C and vitamin E in sufficient amounts so as to raise the concentration of said vitamins in blood plasma sufficiently and to a controlled ratio wherein said vitamin C is formulated in a slow-release preparation and vitamin E is formulated in plain-release formulation.

Furthermore, the invention relates to the use of a combination of vitamin C. and vitamin E for the preparation of a drug or drug system for treating or preventing atherosclerosis or other diseases or conditions responsive to antioxidants, wherein said vitamins are incorporated in the patients blood plasma in high concentrations and in a controlled ratio characterised in that the drug or drug system has a slow release of vitamin C and a normal release of vitamin E.

DETAILED DESCRIPTION

Figure 1:
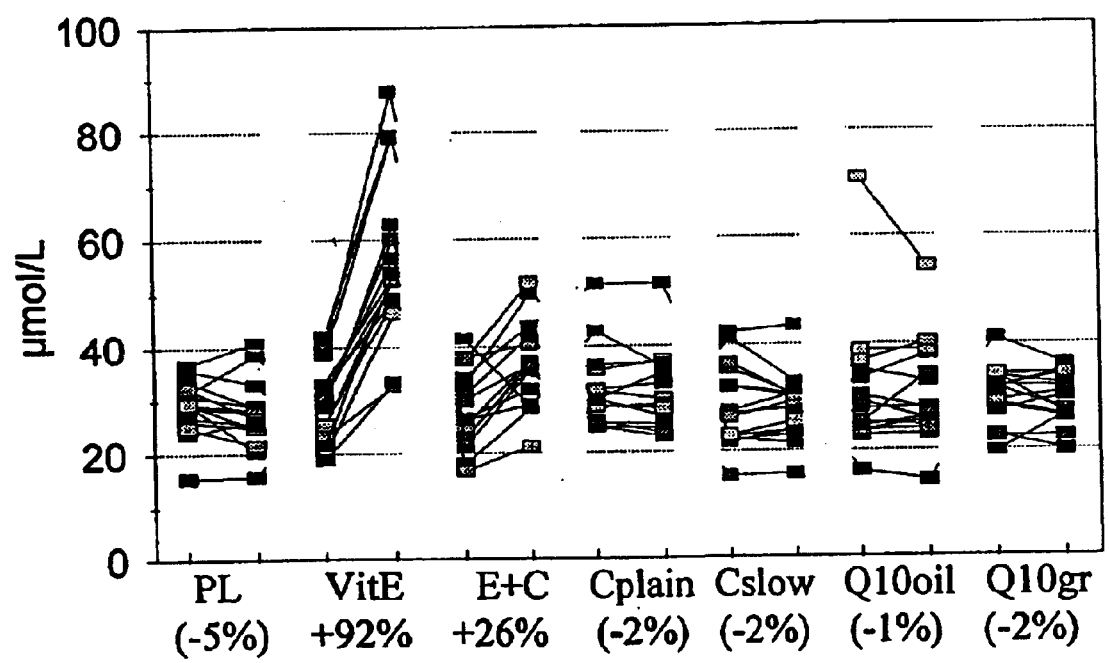
FIG. 1 summarizes the plasma vitamin E concentrations in the Masi study at baseline and after two months supplementation.

Early studies by the present inventors showed that slow release vitamin E combined with vitamin C gave poor bioavailability of vitamin E compared to a conventional vitamin E formulations. It was shown that if vitamin E (α-tocopheryl acetate) is mixed into the sustained release vitamin C matrix, vitamin E is not absorbed very well (15).

Surprisingly, It was found by the present inventors that the preferred delivery system comprising a slow release of vitamin C and plain release of vitamin E provides a high, constant concentration of the vitamins in the blood of a human in need of the vitamins. Furthermore, it was found that said delivery system provided vitamins C and E in a ratio and at plasma concentrations surprisingly effective for oxidative resistance.

Herein, a formulation is disclosed wherein a vitamin E matrix is plainly released, and vitamin C is slowly released thus providing the desired and optimum plasma vitamin C and E concentrations over time. Thus, contrary to Salonen (15), vitamin E in the formulation of the present invention given in a conventional tablet was found to be well absorbed. Vitamin E is therefore to be administered in a form for plain release such as a conventional tablet, which disintegrates within 30 minutes, making vitamin E accessible for absorption.

It is one object of the invention to provide a delivery system for oral delivery of vitamin C and vitamin E to obtain high concentrations thereof and a controlled ratio between vitamin C and vitamin E in blood plasma in humans or animals, characterised in that it has a slow release formulation of vitamin C and a plain release formulation of vitamin E.

As stated, vitamin E and vitamin C are considered two of the most important dietary antioxidants. Vitamin E may also have other anti-atherogenic properties. When vitamin E works as an antioxidant it is oxidised to harmful α-tocopheroxyl radical, which needs to get reduced back to α-tocopherol. Vitamin C can regenerate α-tocopheroxyl radical to (αtocopherol.

The term "slow release formulation" is intended to mean a formulation whereby the tablets thereof are coated or uncoated containing excipients or prepared by special procedures which, separately or together, are designed to modify the rate or the place at which the active ingredient is released, as is defined by the US Pharmacopoeia for modified-release tablets. Specifically, the term used herein is intended to mean a formulation within the threshold of dissolution in vitro as defined by Test A described herein.

The term "plain release formulation" is intended to mean a formulation whereby the tablets thereof are designed to release at least 90% of vitamin E within 30 minutes in vitro under conditions of Test B. According to the US Pharmacopoeia, tablets without modified release are to disintegrate within 60 minutes. For nutritional supplements, according to the US Pharmacopoeia, tablets without modified release, should release at least 75% of the index ingredient within 60 minutes.

The term "vitamin C" is intended to mean ascorbic acid equivalents such as salts of the ascorbate such as sodium ascorbate, calcium ascorbate and ascorbyl palmitate.

The term "vitamin E" is intended to mean α-tocopherol equivalents and may be, for example, any natural or synthetic vitamin E chosen from the group comprising d-α-tocopheryl acetate, d-α-tocopheryl acid succinate, d-β-tocopherol, d-β-tocopherol, d-γ-tocopherol, d-δ-tocopherol, d-α-tocotrienol, d-β-tocotrienol, d-γ-tocotrienol, d-δ-tocotrienol, dl-α-tocopherol, dl-α-tocopheryl acetate, dl-α-tocopheryl calcium succinate, dl-α-tocopheryl nicotinate, dl-α-tocopheryl linoleate/oleate and all other possible stereo isomeric forms of the above compounds.

The present invention seeks to provide a method of providing oxidation resistance without the use of and β-carotene or selenium by providing high concentrations of vitamin C and E at a controlled ratio in blood plasma.

The present invention solves the problem of providing high concentrations of vitamin C and E in the preferred ratio by using a pharmaceutical delivery system for oral delivery of vitamin C and vitamin E in order to obtain high concentrations thereof in a controlled ratio in blood plasma in humans or animals by a delivery system with slow release of vitamin C and plain release of vitamin E.

The present invention is based on the notion that a certain ratio between vitamin C (ascorbic acid) and vitamin E (α-tocopherol) is necessary for optimum protection of LDL particles.

The system of the invention provides a ratio of concentrations between vitamin C and vitamin E in the blood plasma from 1:5 to 5:1, preferably from 1:1 to 3:1. The amount of vitamin C is preferably higher than that of vitamin E. The most preferred ratio is 2.2:1.

This ratio, as measured in the blood plasma 8 weeks from the onset of a regimen comprising the at least once daily oral administration of the delivery system, is achieved no more than 8 weeks from the onset of said regimen, such as no more than 7, 6, 5, or 4 weeks. The present inventors have found a steady state is achieved in the blood plasma of vitamins C and E in the desired ratio, by means of measurements taken anytime after 8 weeks. Once the ratios achieved, the ratio is maintained for at least as long as the regimen is followed. Measurements taken 3 years from the onset of a regimen showed similar ratios as measurements taken 8 weeks from the onset of the regimen.

Upon administration of the delivery system, the concentration of vitamin E in human blood plasma, measured no more than 8 weeks from the onset of a regimen comprising the at least once daily oral administration of the delivery system, should be raised to at least 20 μmol/liter, preferably at least 30 μmol/liter, such as at least 40 or 50 μmol/liter, preferably at least 55 μmol/liter, and the concentration of vitamin C to at least 40 μmol/liter preferably at least 60 μmol/liter, such as at least 70, 80, 90 μmol/liter, preferably at least 100 μmol/liter. Using the delivery system of the invention, it has been possible to reach a concentration of vitamin C of about 180 μmol/liter and a concentration of vitamin E of about 180 μmol/liter. Examples of concentrations preferred for each of the vitamins concomitantly present in the blood plasma are 180 μmol/liter vitamin C and 81.8 μmol/liter vitamin E; 160 μmol/liter vitamin C and 72.7 μmol/liter vitamin E; 140 μmol/liter vitamin C and 66.6 μmol/liter vitamin E; 120 μmol/liter vitamin C and 54.5 μmol/liter vitamin E; 100 μmol/liter vitamin C and 45.5 μmol/liter vitamin E; 80 μmol/liter vitamin C and 36.4 μmol/liter vitamin E; 70 μmol/liter vitamin C and 31.8 μmol/liter vitamin E; 80 μmol/liter vitamin C and 27.3 μmol/liter vitamin E; 50 μmol/liter vitamin C and 22.7 μmol/liter vitamin E. Most preferably, the relative concentrations of vitamins C and E concomitantly present in the blood plasma are from about 102 to about 142 μmol/liter and from about 46 to about 65 μmol/liter, respectively, such as 112 μmol/liter of vitamin C and 51 μmol/liter of vitamin E, 122 μmol/liter of vitamin C and 55.5 μmol/liter of vitamin E, 132 μmol/liter of vitamin C and 60 μmol/liter of vitamin E, or 142 μmol/liter of vitamin C and 65 μmol/liter of vitamin E, especially preferred concentrations of the vitamins in human blood plasma are 132 μmol/liter of vitamin C and 60 μmol/liter of vitamin E.

These concentrations, as measured in the blood plasma 8 weeks from the onset of a regimen comprising the at least once daily oral administration of the delivery system, are achieved no more than 8 weeks from the onset of said regimen, such as no more than 7, 6, 5, or 4 weeks. The present inventors have found a steady state is obtained in the blood plasma of the concentrations of vitamins C and E by means of measurements taken anytime after 8 weeks. Once the concentrations achieved, they are maintained for at least as long as the regimen is followed. Measurements taken 3 years from the onset of a regimen showed the same concentrations as measurements taken 8 weeks from the onset of the regimen.

These ratios or concentrations may be achieved by administration of a daily dose of at least 1 dosage unit. Depending on the number of dosage units administered to achieve the daily dose according to the invention, the amount of each of the vitamins in each of the dosage units will quite obviously vary. Preferably, at most 8 dosage units are administered for each daily dose, such as at most 4 dosage units, at most 3 dosage units, at most 2 dosage units, at most 1 dosage unit. In the most preferred embodiment, 1 or 2 dosage units are administered to achieve the daily dose, most preferably 2 dosage units.

The daily dose of each of the vitamins corresponds to 60 mg–2 g of vitamin C and 10 mg–800 mg of vitamin E. Preferably, the daily dose of vitamin C is a dose corresponding to 100 mg–1.5 g of ascorbic acid, such as 200 mg–1 g, most preferably corresponding to 250 mg–750 mg of ascorbic acid, preferably 300 mg–600 mg, particularly corresponding to 500 mg of ascorbic acid. Preferably, the daily dose of vitamin E is a dose corresponding to 50 mg–500 mg of α-tocopherol, such as 100 mg–250 mg, most preferably corresponding to 150 mg–200 mg of α-tocopherol, preferably 175 mg–190 mg, particularly corresponding to 180–185 mg of of α-tocopherol, such as 180, 181, 182, 183, 184 or 185 mg, preferably 182 mg.

As stated, the daily dose of each of the vitamins is most preferably achieved by the daily administration of 2 dosage units. In this embodiment of the invention, each dosage unit comprises i) at most 1 g of vitamin C, such as at most 500 mg such as at most 400 mg, 300 mg, preferably 250 mg of vitamin C and ii) at most 400 mg of vitamin E, such as at most 300 mg, 200 mg or 150 mg, preferably about 100 mg, such as 90 mg, 91 mg, 92, 93, 94, 95, 96, 97, 98, 99, or 100 mg of vitamin E.

In a preferred embodiment of the invention, the delivery system comprises a daily dose corresponding to 500 mg of vitamin C in a slow release formulation and 182 mg of vitamin E in a plain release formulation. In a most preferred embodiment of the invention, the delivery system comprises a dosage unit formulation administered twice daily comprising 250 mg of vitamin C in a slow release formulation and 91 mg of vitamin E in a plain release formulation.

In an alternative embodiment of the invention, the delivery system may comprise of dosage units with non-identical amounts of the vitamins such that a dosage unit comprises substantially all of the daily dose of vitamin C and only a fraction of the vitamin E daily dose and one or more dosage units to be administered during the day comprise the remaining fractions of the daily dose of vitamin E and is/are substantially devoid of vitamin C. Conversely, the delivery system may comprise of dosage units with non-identical amounts of the vitamins such that a dosage unit comprises substantially all of the daily dose of vitamin E and only a fraction of the vitamin C daily dose and one or more dosage units to be administered during the day comprise the remaining fractions of the daily dose of vitamin C and is/are substantially devoid of vitamin E.

The ratios or concentrations of vitamin C and vitamin E can be achieved by a number of types of dosage units such as tablets. The delivery system may comprise of dosage units formulated for oral administration such as a hard or chewable tablet. capsule, granulates or powders so long as the system is characterised by slow release of vitamin C and plain release of vitamin E. Powders or granulates for example, may be powdered or granulated blends of the a formulation of vitamin C and a formulation of vitamin E in one sachet or in separate sachets. Similarly, capsules may comprise each of the two formulations.

A further object of the present invention is to provide a delivery system to obtain a controlled increase in blood plasma levels of both vitamin C and E, as measured after 8 weeks. Levels of the vitamins, according to concomitant measurements, preferably increase from 50 to 100% for vitamin E, such as from 60 to 80%, preferably from 70 to 80%, and from 30 to 80% for vitamin C, such as from 40 to 70%, preferably from 40 to 65%. In one embodiment of the invention, the high concentrations of vitamin C and E, as measured after 3 years of administration of the system according to the present invention, were such that to equate to an increase of about 71% to 76% in blood plasma vitamin E and an increase of about 46% to 60% of vitamin C (see Table 4). It is understood that these increases of plasma levels are the result of the delivery system according to the present invention without the assistance of supplementation of β-carotene or selenium either of which can on their own contribute to high levels of at least vitamin E.

The system can be a pharmaceutical delivery system comprising a tablet comprising two or more different delivery principles, wherein (A) one delivery principle comprises (i) vitamin C (ii) a pharmaceutically acceptable excipient for controlling the slow release of vitamin C, (iii) other pharmaceutically acceptable excipients (B), another delivery principle comprises (i) vitamin E (ii) pharmaceutically acceptable excipients.

In a preferred embodiment of the invention, the system is a the tablet comprising two layers whereby vitamin C is in one layer and vitamin E is in the other layer. However, the delivery system of the invention can be any system providing a high concentration of vitamin C and vitamin E at the same time in the blood.

The system can of course be any known delivery system providing slow release of vitamin C and plain release of vitamin E.

It is known that absorption of vitamin C improves when the active Ingredients are released from the tablet in a manner making it accessible for absorption over a period of 7–9 hours (16). This type of formulation is called a sustained release formulation and is also known as an extended release formulation, a prolonged release formulation, a slow release formulation and a modified release formulation.

The formulation of vitamin C in the delivery system according to the present invention preferably is such that less than 40% of vitamin C is dissolved after 1 hour under the conditions of Test A, from 50 to 80% of vitamin C is dissolved after 3 hours under the conditions of Test A, and more than 90% of vitamin C is dissolved after 7 hours under the conditions of Test A.

Sustained release formulations are known to give lower peak values than other administration forms, but keep the desired plasma level for a longer time (17). With repeated dosages of the sustained release formulation, a much more constant plasma level may be obtained compared to conventional tablets.

Sustained release formulation can be achieved by different techniques, such as matrix tablets, erosion tablets, lattice tablets, or by coating of the tablet or the active ingredient.

Sustained release formulations for oral use may be constructed to release vitamin C by controlling the dissolution of vitamin C, its diffusion or both. Dissolution or diffusion controlled release may be achieved by appropriate coating of a tablet capsule, pellet or granulate formulation of vitamin C.

The matrix principle, which is a preferred embodiment of the tablet formulation for vitamin C, is achieved by mixing the active ingredient with hydrocolloid macromolecular excipients in large amounts, typically more than 25%. When ingested, the tablet forms a highly viscous gelatinous mass at the surface maintaining the shape of the tablet. The active component is slowly released from the surface of the gelatinous mass, at a rate which is controlled by its diffusion through the gel-barrier.

The following macromolecular excipients can be used for creating this gel: methylcellulose, hydroxypropyl methylcellose, carboxymethyl starch or other modified cellulosic substances, hydrophilic gums such as pectinates or alginates.

Erosion tablets differ from the matrix tablet in that the excipients used are lipids, which will not dissolve or gel in the stomach, but slowly be eroded, thus releasing the active ingredient The following lipids are frequently used for this purpose: stearic acid, glycerol monostearate, stearyl alcohol, cetyl alcohol, and hydrogenated fats.

Lattice tablets differ from the former types in that the excipient chosen is insoluble in the stomach. The tablet will therefore not disintegrate, and the active ingredient is released by diffusion, leaving the lattice unchanged. As excipients for lattice tablets, polyvinyl acetate, polyvinyl chloride or polyethylene may be used.

As stated, the sustained release effect can also be achieved either by coating the tablet or by coating the active particles or pellets made herefrom (micros encapsulation). The coating must be made of an insoluble polymer, whereby the active ingredient must traverse by diffusion. As polymers for film coating, ethyl cellulose, polymethacrylates or lipids may be used. Alternatively, a sustained release coating may be selected from coatings comprising cellulose derivatives such as hydroxypropyl methylcellulose, methylcellulose, methylhydroxycellulose, methylhydroxyethyl cellulose, hydroxypropyl cellulose, carboxymethylcellulose, cellulose acetate, cellulose propionate, cellulose butyrate, cellulose valerate, cellulose acetate propionate and cellulose acetate butyrate; acrylate polymers such as acrylic resins, polymethylacrylate, methylmethacrylate, 2-hydroxymethacrylate, polyethylene glycol methacrylate, methacrylate hydrogels; vinyl polymers such as polyvinyl chloride, polyvinyl acetate, vinyl pyrrolidine, polyvinyl pyrrolidone, polyvinyl formal, polyvinyl butyryl, vinyl chloride-vinyl acetate coplymer, vinyl chloride-propylene-vinyl acetate copolymer; silicon polymers such as ladder polymer of sesquiphenyl siloxane and colloidal silica; waxes such as shellac, beeswax, glycowax, castor wax, beef tallow, whale wax, parrafin wax, and canauba wax; stearic acid derivatives and esters such as stearyl alcohol, glyceryl monostearate, glyceryl distearate, glycerol palmitostearate; myristic acid derivatives and esters, palmitic acid derivatives and esters, behinic acid derivatives and esters, dl-polylactic acid; polyethylene; and/or 1,3-butylene glycol.

The coating may be admixed with various excipients such as plasticizers and anti-adhesives such as colloidal silicum dioxide, flavouring agents, lubricating-agents and pigments in a manner known to the person skilled in the art.

Tablet strengthening agents, such as silica, may also be added to the formulation as may binding agents, inert fillers, flavouring agents or lubricating agents.

In a interesting embodiment of he delivery system, vitamin C is formulated for sustained release by a matrix principle in at least one layer of a tablet whereas vitamin E is released plainly or immediately from a non-identical layer of the tablet In such embodiments, a tablet may comprise of at least two non-identical layers wherein vitamin C is comprised within at least one layer and vitamin E is comprised within at least one non-identical layer. Alternatively, a vitamin E layer may enrobe or surround substantially the entire vitamin C layer.

In a preferred embodiment, the formulation is of a tablet in the matrix technique with hydroxypropyl methylcellulose as the gel forming excipient. This results in a release profile relatively low in sensitivity to differences in production parameters.

Figure 2:
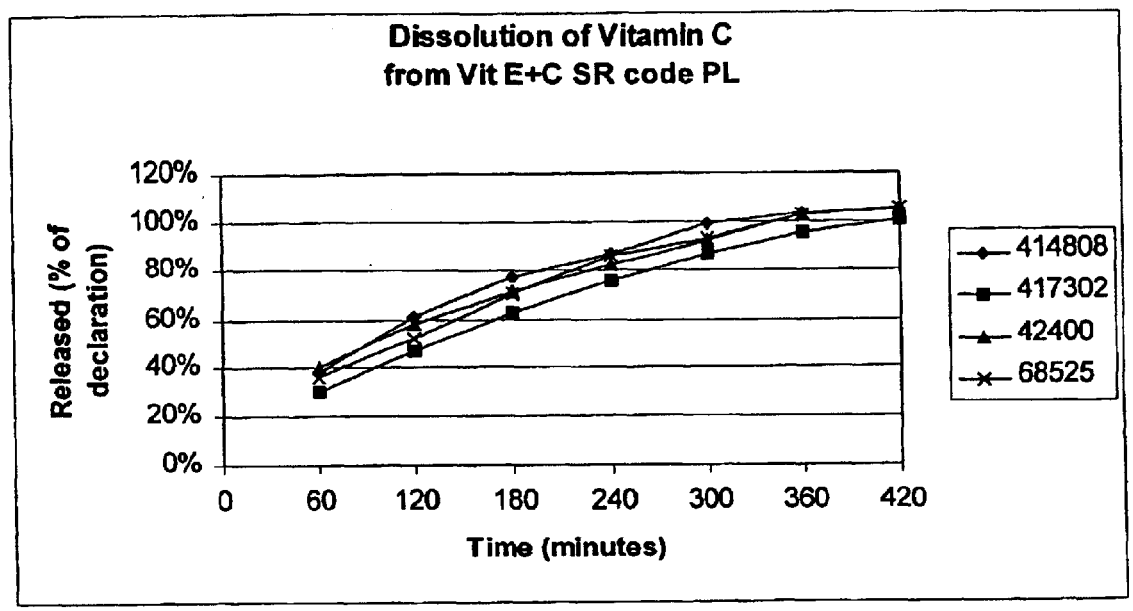
FIG. 2 shows comparative vitamin C release profiles.

FIG. 2 shows the release pattern measured on different batches. The graph of FIG. 2 demonstrates that vitamin C is released over 7 hours, and that the production process is reproducible in relation to release of vitamin C.

Likewise, it is expected that making the vitamin C sustained release by other hydrocolloids (as those described earlier) or any other technique (as those described earlier) will have the same effect on the absorption of the product.

Vitamin C may be selected from ascorbic acid itself or a derivative or a salt thereof, such as sodium ascorbate, calcium ascorbate or ascorbyl palmitate.

The delivery system according to the present invention is characterised in part by a slow release formulation of Vitamin C. According to one aspect of the invention, the delivery system comprises a bi-layer tablet formulated with vitamin C and vitamin E. The vitamin E layer is preferably formulated as a conventional tablet meeting the normal requirements for disintegration.

In a preferred embodiment, the formulation comprises ascorbic acid and d-α-tocopheryl acetate as sources for the active components.

Figure 3:
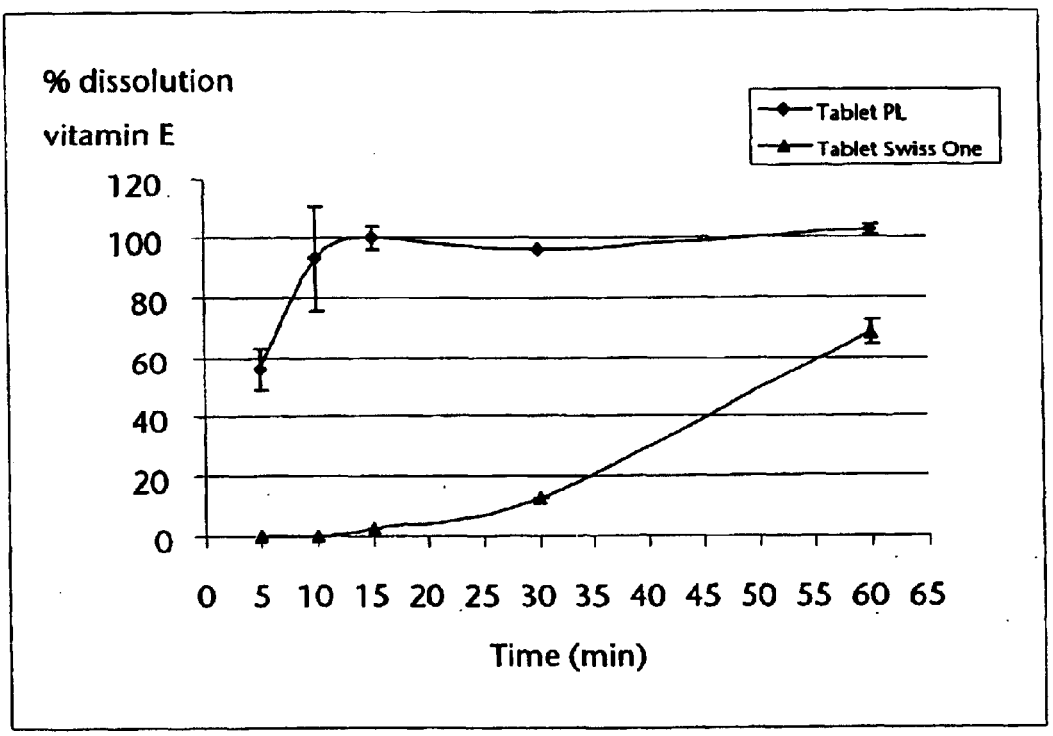
FIG. 3 shows comparative vitamin E release profiles.

The delivery system according to the present invention is characterised in part by a plain release of vitamin E. In preferred embodiments, the formulation of vitamin E is such that the tablet or moiety of the tablet comprising vitamin E, releases vitamin E in vitro within 30 minutes by at least 90% under conditions of Test B, preferably within 15 minutes. FIG. 3 depicts the degree of dissolution of a preferred embodiment of the present invention wherein the percentage of release of vitamin E as a function of time is depicted and compared to a formulation with sustained release of vitamin E.

The preferred in vitro release profile in order to provide the appropriate ratio of vitamins C and E with the appropriate concentration in blood plasma is such that less than 40% of vitamin C is dissolved within 1 h and at least 90% of vitamin E is dissolved within 30 minutes. Table 3 shows the release profile of products currently on the market. Even those products which comprise additional antioxidants do not have the preferred release profile to achieve the desired result. FIG. 3 demonstrates the release profile for vitamin E of a preferred embodiment of the invention. Furthermore, it compares the profile of a product which had a similar release profile for vitamin C with the preferred profile according to Table 3. The graph clearly demonstrates that despite the similarity after 60 minutes, the profile is markedly different and does not reach the preferred release of at least 90% after at most 30 minutes, such of at least 90% after at most 15 minutes for vitamin E.

The present investigators have found that a delivery system according to the present invention and the resultant blood plasma concentration and ratios of vitamin C and E performed well during in vivo studies. Particularly, the system according to the present invention was found to be beneficial for prevention/treatment of oxidative stress related indications.

The present inventors conducted experiments which have as at least one objective the study of the effect of reasonable supplemented doses of vitamin E and vitamin C and their combination on the progression of common carotid atherosclerosis in C) middle-aged high-risk men and women in three years. As men and cigarette smokers are at enhanced oxidative stress and lipid peroxidation (18, 23), a greater atherosclerotic progression retarding effect was hypothesised a priori in men and in smokers than in women and in non-smokers. Because of the synergism between vitamin E and vitamin C in the human body, the greatest protective effect was hypothesised by the combined supplementation.

Thus, an object of the invention is the use of a combination of vitamin C and vitamin E for the preparation of a drug, drug system or delivery system for treating or preventing oxidative stress related indications wherein said vitamins are incorporated in the patients blood plasma in high concentrations and in a controlled ratio, characterised in that the drug has a slow release of vitamin C and a normal release of vitamin E.

A further object to of the invention is the use of a delivery system as described herein for the prevention/treatment of oxidative stress related indications such as atherosclerosis or other diseases or conditions responsive to antioxidants. An object of the invention is thus the use of a combination of vitamin C and vitamin E for the preparation of a delivery system for the treatment or prevention of atherosclerosis, cancer, type I and type II diabetes and diabetic nephropathy, for skin repair and scar tissue formation, for the protection or treatment against central nervous system disorders and degeneration and neural degeneration in general such as for example in Alzheimer's Disease, for anti-inflammatory effects, for improvements in fertility/fecundity, for protection against the effects of the sun, for the treatment or prevention of cataracts, for anticoagulation, or as an antidote for nitrate-tolerance.

The system according to the present invention may alternatively be used for patients having vitamin C and/or E deficiency, but especially for preventing or treating conditions or diseases involving oxidative stress, such as arteriosclerosis, cancer, cataract, diabetes I and II, and ageing. Many human studies have been performed in these areas regarding the role of vitamins E or C in these conditions relating to oxidative stress from endogenous or exogenous sources.

A further object of the invention is to provide a method of treating or preventing oxidative stress disorders and associate diseases comprising the administration to an individual a combination of vitamin C and vitamin E in sufficient amounts so as to raise, within 8 weeks of the first administration, the concentration of said vitamins in blood plasma sufficiently and to a ratio of from 1:1 to 3:1, preferably 2.2:1.

Furthermore, the invention provides method of treating or preventing oxidative stress disorders and associate diseases comprising the daily administration to an individual at least one dosage unit comprising a combination of vitamin C and vitamin E in sufficient amounts so as to raise the concentration of said vitamins in blood plasma sufficiently and to a controlled ratio wherein said vitamin C is formulated in a slow-release preparation and vitamin E is formulated in plain-release formulation.

Preferably, the blood plasma concentrations are raised sufficiently or to the preferred ratio at most 8 weeks from the first administration, such as at most 7 weeks of the first administration, such at most 6 weeks, preferably at most 5 weeks, most preferably at most 4 weeks.

In a preferred embodiment of a method of the present invention, at most 8 weeks from the first administration, the blood plasma concentration of vitamin E is at least 20 $\mu$mol/liter, preferably at least 30 $\mu$mol/liter, such as at least 40 or at least 50 $\mu$mol/liter, most preferably at least 55 $\mu$mol/liter and the concentration of vitamin C is raised to at least 40 $\mu$mol/liter, preferably at lease 60 $\mu$mol/liter, such as at least 70, 80, 90 $\mu$mol/liter, most preferably at least 100 $\mu$mol/liter. Most preferably, the concentrations of vitamins C and E concomitantly present in the blood plasma are from 102 to about 142 $\mu$mol/liter and from about 46 to about 65 $\mu$mol/liter, respectively, such as 112 $\mu$mol/liter of vitamin C and 51 $\mu$mol/liter of vitamin E, 122 $\mu$mol/liter of vitamin C and 55.5 $\mu$mol/liter of vitamin E, 132 $\mu$mol/liter of vitamin C and 60 $\mu$mol/liter of vitamin E, or 142 $\mu$mol/liter of vitamin C and 65 $\mu$mol/liter of vitamin E, especially preferred concentrations of the vitamins in human blood plasma are 132 $\mu$mol/liter of vitamin C and 60 $\mu$mol/liter of vitamin E.

In another embodiment of a method of the invention, the administration is of an at least once daily dose of dosage units comprising slow release formulation vitamin C and plain release vitamin E, preferably at most 8 dosage units, such as at most 6 dosage units, such as at most 5 dosage units, such as 4, 3, 2, or 1, preferably 2 or 1, most preferably 2 dosage units.

The method of the invention preferably comprises dosage units wherein the slow release formulation releases less than 40% of vitamin C after 1 hour under the conditions of Test A, from 50 to 80% of vitamin C is released after 3 hours under the conditions of Test A, and more than 90% of vitamin C is dissolved after 7 hours under the conditions of Test A and the plain release formulation releases at least 90% of vitamin E is dissolved in less than 30 minutes under the conditions of Test B, such as in less than 15 minutes.

The method of the invention preferably comprises the daily dose of vitamin E corresponding to 50 mg–500 mg of $\alpha$-tocopherol, such as 100 mg–250 mg, most preferably to 150 mg–200 mg of $\alpha$-tocopherol, preferably 175 mg–190 mg, particularly corresponding to 180–185 mg of $\alpha$-tocopherol, most preferably 182 mg.

Similarly, the method of the invention preferably comprises the daily dose of vitamin C corresponding to 100 mg–1.5 g of ascorbic acid, such as 200 mg–1 g, most preferably corresponding to 250 mg–750 mg of ascorbic acid, preferably 300 mg–600 mg, particularly corresponding to 500 mg of ascorbic acid.

In the preferred embodiment wherein the daily dose of vitamin C and E is delivered by 2 dosage units, each dosage unit preferably comprises i) from approximately 200 to 300 mg of vitamin C, such as 200, 225, 250, 275, or 300 mg, preferably 250 mg of vitamin C and ii) approximately 80 to 120 mg of vitamin E, such as from 80 to 100 mg preferably about 90 mg, such as 91 mg, 92, 93, 94, 95, 96, 97, 98, 99 mg of vitamin E, preferably 91 mg.

The invention is further disclosed by the examples infra which are not intended to be limiting in any way.

EXAMPLES

Example 1

Masi Study

In this study, the inventors found that slow release vitamin E combined with slow vitamin C, in a similar test, gives poor bioavailability of vitamin E compared to a conventional vitamin E formulation.

FIG. 1 summarises the plasma vitamin E measurement in the MASIstudy (13) at baseline and after two months supplementation. This figure shows the results of plasma vitamin E concentrations before and after 8 weeks supplementation with 7 different treatments. PL depicts placebo; VitE depicts a tablet with 91 mg vitamin E in normal release formulation; E+C depicts a dosage unit with 250 mg vitamin C in a slow release formulation plus 91 mg vitamin E in a slow release formulation; Cplain is a plain formulation of vitC; Cslow is a formulation of slow release vitC, $Q_{10}$oil is Coenzyme $Q_{10}$ formulated in oil, $Q_{10}$gr is Coenzyme $Q_{10}$ in granulate formulation. Cplain, Cslow, Q10oil and Q10gr are all formulations not containing vitamin E and can be regarded as non placebo controls.

The data shows that the bioavailability of vitamin E in a vitamin E plus C slow release formulation (E+C) is much less than from a plain release formulation (VitE). No statistically significant increases in plasma vitamin E levels were observed for the placebo control and the non-placebo controls. Significant increases of vitamin E were observed in the vitE sample whereas only small increase were observed in the E+C sample. On the basis of these findings, a delivery system was developed such that a dosage unit, such as a tablet, comprising of vitamin E in a matrix designed to give plain release, as in the vitE formulation, and of vitamin C in a matrix designed to give slow release, since this provided more even plasma vitamin C concentrations over time.

Example 2

A tablet according to the invention was prepared as follows:

| Active ingredients: | Vitamin E | 91 mg |
|---|---|---|
| | Vitamin C | 250 mg |

Tablets were prepared as follows:

Vitamin E as 102 kg De-$\alpha$-tocopherol acetate concentrate powder form) was mixed with Silica, Colloidal Anhydrous (5–15 kg) and microcrystalline cellulose (50–100 kg). Magnesium stearate (approx. 1 kg) was added and mixed again.

Vitamin C as 135 kg Ascorbic Acid 97% was mixed with hydroxypropyl methylcellulose K100 M (50–100 kg). Magnesium stearate (approx ¼–½ kg) was added and mixed again.

Bi-layered tablets with the Vitamin E mix as one layer and the Vitamin C mix as the second layer were compressed at 12 mm tooling.

FIG. 2 shows the release pattern for Vitamin C measured on different batches and FIG. 3 the release pattern for Vitamin E measured on one batch.

Example 3

Dissolution

Vitamin C (Test A)

Test A conforms with the European Pharmacopeia regulation 711 Dissolution to determine the dissolution for a tablet or capsule. Apparatus 2 of the regulation was employed with the following specifications:

| | |
|---|---|
| Rotation speed | 50 rpm |
| Medium | 1000 mL of 0.1 N hydrochloric acid |
| Sampling volume | 10.0 mL |

Correction for degradation during dissolution was used

Method of analysis spectrophotometric measure of absorbance at 244 nm.

Result

| | |
|---|---|
| dissolution after 1 hour: | less than 40% |
| dissolution after 3 hours: | from 50% to 80% |
| dissolution after 7 hours: | more than 90% |

Vitamin E (Test B)

Test B comprised of the use of an apparatus wherein a glass flask on a heated (37° C.) water bath containing 15 mL of water. At the prescribed timepoints, the dissolution media was transferred to a clean flask. The first flask with the rest of the tablet was washed with 25 mL ethanol (99%). The ethanol was decanted to the second flask containing the dissolution media. Vitamin E was assayed by gas chromatographic procedures known to the person skilled in the art. The test was run in duplicate.

TABLE 3

Dissolution profiles of products on the mark t in comparison to pref rred profile

| | Vitamin E | | Vitamin C | |
|---|---|---|---|---|
| Product Name | IU/tablet | % dissolution 60 min | mg/tablet | % dissolution after 50 min |
| Preferred | 80–120 | at least 90 | 200–300 | less than 40 |
| Swiss/β-carotene + C + E + Selen | 400 | 99.4 | 250 | 4.3 |
| Aces/β-carotene + C + E + Selen | 200 | 119 | 350 | 60 |
| Ferrosen/Oxi-Tabs | 130 | 15 | 200 | 26 |
| PRN/Ultimate Multi-vitamins | 130 | 82 | 167 | 102 |
| Hi Potency Swiss One "80" | 100 | 91 | 250 | 30 |
| Quest/β-carotene + C + E + Selen | 100 | 109 | 500 | 128 |
| Champion Nutrition Oxi-Pro | 100 | 97 | 250 | 60 |
| Super Swiss One "50" | 75 | 0 | 100 | 46 |
| Seroyal/super Orti Vite | 75 | 110 | 100 | 110 |
| Am. Health/More than a Multiple | 67 | 0 | 167 | 1 |
| TwinLab/DualTabs | 50 | 17 | 250 | 38 |
| Essentially All | 33 | 102 | 250 | 74 |
| Multi Vitamin Energy Plus | 15 | 100 | 110 | 113 |
| Swiss One | 10 | 97 | 100 | 73 |

Example 4

Clinical Results

The inventors conducted a controlled trial with a formulation including both slow release vitamin C and conventional release vitamin E (250 mg AA and 91 mg α-tocopherol). 520 men and women, smokers and non-smokers, were randomised to vitamin C slow release, vitamin E, a formulation with vitamin E and slow release vitamin C, or placebo (Table 4). The combined formulation gave a 72–89 percent increase in plasma vitamin E and a 60–72 percent increase in plasma vitamin C in plasma (morning values).

In men, the mean plasma (α-tocopherol concentration increased in the placebo group from 31.0 to 33.2 µmol/L (by 7.2%), in the vitamin E group from 31.7 to 60.1 µmol/L (by 89.2%), in the vitamin C group from 32.3 to 33.9 µmol/L (by 5.1%) and in the group randomised to both vitamins from 32.1 to 55.2 µmol/L (by 71.9%). The respective changes of plasma total ascorbate concentration were −5.0, 3.8, 71.5 and 59.9%. In women, plasma α-tocopherol concentration increased in placebo, vitamin E, vitamin C and double vitamin groups by 5.6, 82.0, 4.0 and 75.4% and plasma total ascorbate by −1.1, 2.5, 47.1 and 46.1%, respectively ($p<0.001$ for heterogeneity for all comparisons).

TABLE 4

Changes in levels of vitamins C and E using one embodiment of the delivery system according to the present invention

| | vitamin E in plasma | vitamin C in plasma |
|---|---|---|
| MALE | | |
| vitamin E group | 31.7 –> 60.1 (89.2%) | +3.8% |
| vitamin C group | 32.3 –> 33.9 (5.1%) | +71.5% |
| placebo group | 31.0 –> 33.2 (7.2%) | 5.0% |
| vit E + C | 32.1 –> 55.2 (71.9%) | +59.9% |
| FEMALE | | |
| Vitamin E group | 82.0% | +2.5% |
| Vitamin C group | 4.0% | +47.1% |
| placebo group | 5.6% | −1.1% |
| vit E + C group | 75.4% | +46.1% |

Example 5

The effect of vitamin E and vitamin C on 3-year progression of carotid atherosclerosis was the goal of the Antioxidant Supplementation in Atherosclerosis Prevention (ASAP) study The favourable effect of a targeted increase in both vitamin C and vitamin E plasma concentrations shown in Example 4 lead the inventors to that conduct experiments which have an objective to study the effect of reasonable supplemented doses of vitamin E and vitamin C and their combination on the progression of common carotid atherosclerosis in middle-aged high-risk men and women in three years. As men and cigarette smokers are at enhanced oxidative stress and lipid peroxidation (18, 23), a greater atherosclerotic progression retarding effect was hypothesised a priori in men and in smokers than in women and in non-smokers. Because of the synergism between vitamin E and vitamin C in the human body, the greatest protective effect was hypothesised by the combined supplementation.

In smoking men, the group with considerable oxidative stress, the progression rate of the thickness of the arteria intima was reduced from 0.020 mm/yr on placebo to 0.011 mm/yr after the combined formulation p<0.05. This corresponds to almost halving the progression of the process that can later manifest itself as arteriosclerosis. The thickness of the carotid intima was measured with ultrasound, this measurement has shown to be predictive of coronary heart disease and may be predictive of other arteriosclerotic manifestations as well.

Introduction

Evidence from both basic research and epidemiology indicates that enhanced lipid peroxidation is associated with accelerated atherogenesis (18–21, 2), whereas that from randomised clinical trials is very limited and controversial. (21–28) While epidemiologic studies suggest that lipid peroxidation might have its greatest relevance in the early phases of atherosclerotic lesion development (2, 18, 19, 21, 24) and that vitamin E may have a protective effect, if any, in clinically healthy persons (29–34), there are no previous studies testing the hypothetical preventive effect of vitamin E on atherosclerotic progression in clinically healthy subjects.

Vitamin E and vitamin C are considered two of the most important dietary antioxidants (21, 23, 33–35). Vitamin E may also have other antiatherogenic properties (36). When vitamin E works as an antioxidant it is oxidised to harmful $\alpha$-tocopheroxyl radical, which needs to get reduced back to $\alpha$-tocopherol. Vitamin C can regenerate $\alpha$-tocopheroxyl radical to $\alpha$-tocopherol (32). Theoretically, supplementing high-risk individuals with high doses of vitamin E alone could even promote rather than reduce lipid peroxidation (38). Also, in our prospective population study, vitamin C deficiency was associated with increased risk of coronary events (39). For these reasons we designed a randomised clinical trial in which both vitamin E and vitamin C were supplemented in a factorial design.

Background:

Dietary and self-selected supplementation of vitamin E has been associated with a reduced incidence of coronary events, but the evidence from randomised clinical trials is controversial. We studied the efficacy of vitamin E and C supplementation on the progression of carotid atherosclerosis, hypothesising an enhanced preventive effect in men and in smokers and synergism between vitamins.

Methods:

In a double-masked 2×2 factorial trial, 520 smoking and non-smoking men and postmenopausal women aged 45–69 years with serum cholesterol $^35.0$ $\mu$mol/L were randomised in these four strata to receive either 182 mg of d-$\alpha$-tocopheryl acetate, 500 mg of slow-release vitamin C daily, both or placebo for three years. Atherosclerotic progression was defined as linear regression slope of the mean ultrasonographically assessed common carotid intima-media thickness (IMT) over time.

Findings:

The average increase of the mean IMT was 0.020 mm/year among men who were randomised to only placebo and 0.018 mm/year in vitamin E, 0.017 mm/year in vitamin C and 0.011 mm/year in the double vitamin group (p=0.009 for E+C vs other men). The respective means in women were 0.016, 0.015, 0.017 and 0.016 mm/year. The proportion of men with progression was reduced by 74% (95% CI 36–89%, p=0.003) by supplementation with both vitamins, as compared with placebo. This protective effect was greatest in smoking men and absent in women.

The study shows that a combined supplementation with reasonable doses of both vitamin E and vitamin C for at least three years can retard the progression of common carotid atherosclerosis substantially in regularly smoking hypercholesterolemic men. This may imply benefits with regard to other atherosclerosis-based events.

Methods

Study Design, Inclusion and Exclusion Criteria and Supplements

The ASAP study was designed to test the main study hypothesis that the supplementation of 45–69-year old smoking and non-smoking men and postmenopausal women with either 200 mg of d-$\alpha$-tocopheryl acetate or 500 mg of vitamin C daily or both will retard the progression of common carotid atherosclerosis, the elevation of blood pressure and the progression of cataracts. This report concerns the effect on atherosclerosis. ASAP is a clinical placebo-controlled double-masked 2×2 factorial trial. All subjects had hypercholesterolemia, defined as serum cholesterol of $^35.0$ mmol/L at screening.

Subjects were not entered Into the trial if they had: premenopause or regular oral estrogen substitution therapy in women, regular intake of antioxidants, acetosalicylic acid or any other drug with antioxidative properties, severe obesity (BMI>32 kg/m$^2$), type 1 diabetes, cataracts extracted bilaterally making opacity assessment impossible, uncontrolled hypertension (sitting diastolic BP>105 mmHg), any condition limiting mobility, making study visits impossible, severe disease shortening life expectancy, or other disease or condition worsening the adherence to the measurements or treatment.

The study consisted of 8-week dietary counseling and placebo lead-in phase and a 3-year double-masked phase, for which the subjects were randomly allocated to either (i) 100 mg of d-$\alpha$-tocopheryl acetate twice daily (272 IU of vitamin E a day), ii) 250 mg slow-release ascorbic acid twice daily, (iii) both d-$\alpha$-tocopheryl acetate and ascorbic acid in a single tablet, or (iv) placebo only. After the double-blind 3-year period, the study is continuing for another three years as an open study. The doses were chosen on the basis of pilot and kinetic studies (13, 15). The subjects were randomised separately in four strata of approximately equal size: (1) smoking ($^35$ cigarettes/day) men, (2) nonsmoking men, (3) smoking postmenopausal women, and (4) nonsmoking postmenopausal women. All subjects gave a written informed consent.

The subjects came to baseline visits and were randomised. Follow-up visits were 6, 12, 18, 24, 30 and 36 months later. Supplements were given, returned tablets were counted and ultrasonographic assessment of common carotid artery (CCA) intima-media thickness (IMT) was carried out at all these seven visits.

Power Analysis

Based on our previous studies (30), we assumed that the placebo group will have an average slope of CCA-IMT increase of 0.03 mm/year. The goal for the sample size was set at 500 randomised subjects (expectedly 125 in each stratum), which was expected to result in 429 participants at the end of the 3-year period at an annual drop-out rate of 5%. A 25% treatment effect was expected, detectable at a=0.05 with power of >0.80 within gender for vitamin E plus C group compared with other treatment groups.

Study Participants

After screening of volunteers in phone, 948 eligible persons were invited to screening, 803 were examined and 660 persons were entered into a 8-week run-in phase. Of these, 520 subjects (256 men and 264 women) were randomised into the trial. In each treatment group, 64 men and 66 women were randomised. Of the 520 participants, 62 subjects (11.9%) dropped out from the trial by the end of three treatment years, and for 458 subjects (88.1%, 225 men, 233 women) the variable for atherosclerotic progression could be constructed.

Assessment of Atherosclerotic Progression

Equipment: Two identical Biosound Phase 2 systems were used (Biosound, Indianapolis, Ind., USA) equipped with a 8–10 MHz annular array transducer, with a measurement precision of 0.03 mm (41). The scannings were videotaped with PAL S-VHS Panasonic AG 7330E VCR.

Scanning (imaging) procedure and videorecording: The ultrasonographic scanning of the common carotid arteries (CCA), the carotid bulbs and the proximal internal carotid artery (ICA) was performed after a supine rest of 10 minutes, the subject in the supine position. Both longitudinal and cross-sectional images were displayed. The scanning was started with a diagnostic examination of entire accessible carotid tree, to find the most severe lesions. Secondly, the site of the greatest IMT at baseline in the CCA far wall was located and scanned thoroughly. This area was scanned from three angles: anterolateral, lateral and posterolateral.

Measurement from videotapes: All IMT measurements (both baseline and follow-up) from videotapes were made at the same site and angle at all examinations of each subject, which was the site with the greatest IMT (in any angle) which was clearly visible at baseline in the far wall of in CCA below the bulb. At this location IMT was measured in diastole for a length of 10 mm (or shorter, if not visible) in one angle for the far wall. Most often this was the distal centimeter of CCA. All IMT measurements were carried out after the 36-month examination.

Ultrasound image analysis: Computer analysis of ultrasound images to measure IMT was performed with a reading station equipped with Data Translation DT 2861 video frame grabber interfaced to a Panasonic AG 7355 VCR. The Prosound software, utilising automated boundary detection, was used. IMT was determined as the average difference at on the average 100 points between intima/lumen and media/adventitia interface (42).

Measurement Variability: Three technicians scanned 10 subjects twice at a weeks' interval in 1995. The videotapes from all scannings were read by one observer. The repeat correlations for the mean CCA-IMT were 0.988, 0.995 and 0.998 and pairwise inter-observer correlations 0.975, 0.983 and 0.995.

Construction of the main outcome variable: Atherosclerotic progression was defined a priori as the linear regression slope of the mean common carotid IMT over six or seven points of follow-up time (0, 6, 12, 18, 24, 30 and 36 months). For 34 subjects, one follow-up was missing. First, the mean CCA-IMT from the right and the left side was averaged, and then the slope was computed across time-specific means.

Other Measurements

Ascorbic acid was stabilised in heparin plasma with metaphosphoric acid immediately after plasma separation, and frozen at −80° C. Combined ascorbic acid and dehydroascorbic acid were determined with an HPLC method (39). Heparin plasma for α-tocopherol was extracted with ethanol and hexane and measured by a reversed phase HPLC method (15). Cholesterol and triglycerides were determined with enzymatic calorimetric methods (30). Serum LDL cholesterol was measured based on precipitation using polyvinyl sulfate and HDL cholesterol after precipitation with magnesium chloride (30). Plasma fibrinogen concentration was determined with a clotting method (30), plasma homocysteine with an HPLC method (44), and serum ferritin by an immunoradiometric assay (Bio Rad, Quantimune, Hercules, Calif.). Dietary intake of foods and nutrients was assessed at baseline by 4-day instructed food recording. Physical activity was assessed by 12-month checked questionaire (43). Blood pressure was measured manually in sitting position after a rest of 10 minutes, three measurements at 3 minutes' intervals.

Statistical Methods

All study participants for whom the main outcome variable was available, were included in the statistical analysis. Analyses were according to the intention-to-treat principle. As the subjects were randomised separately in four strata (smoking men, non-smoking men, smoking women, non-smoking women), this stratification was maintained also in the statistical analysis. As the a priori power calculations were based on stratified analysis in men and women, the primary statistical analysis was done in these two strata (Table 6).

To test the consistency of results, the outcome variable, the slope of the mean CCA-IMT over all available follow-up assessments, was used both as a continuous variable in general linear models and as a dichotomous variable in logistic models. The cut-off for the dichotomisation was the median among all 225 men. The use of gender-specific cut-off did not influence the results. Odds ratios were estimated as antilogarithms of coefficients and their confidence intervals (Cl) based on normality assumption of SPSS 8.0 for Windows.

Three dummy variables were constructed to indicate whether the participant was randomised to receive only vitamin E, only vitamin C or both vitamins, and these were entered jointly in logistic models. The comparisons in the linear models were between each treatment group and all other groups.

As the distribution of the slope of mean CCA-IMT was not perfectly normally distributed, we used non-parametric methods to test the significance of the heterogeneity (Kruskal-Wallis variance analysis) of outcome between the four treatment groups and the difference between the groups randomised to both vitamins and others (Mann-Whitney test). In spite of one-sided hypotheses, p-values are reported as two-sided.

Results

Adverse Events, Compliance and Adherence to Treatment

Six study participants died during the first three study years. All of these were men. In the placebo group, there was one death due to cardiac arrhythmia. In the vitamin group there were three deaths, of which one was accidental, one due to alcohol intoxication and one sudden coronary death. One man in the vitamin C group died of subarachnoid haemorrhage and one man in the double vitamin group due to complications of carotid endarterectomy.

The distribution of the 62 drop-outs according to the cause of drop-out and treatment group is presented in Table 5 separately for men and women in the randomised groups. There were no differences between the randomised groups.

On the basis of count of returned tablets, during the whole trial on the average 94.9% of tablets were used, with almost no differences between either strata or treatment groups.

Baseline Characteristics

The distributions of the main baseline characteristics of male and female study participants are shown in Table 6. The smoking men had lower serum total, LDL and HDL cholesterol, plasma total ascorbate, α-tocopherol and b-carotene concentrations and greater both baseline mean IMT and increase of the mean IMT in three years (not shown) than the other groups. Both smoking men and smoking women had lower dietary vitamin C intake and higher dietary saturated fat intake and plasma fibrinogen than the non-smokers. Of smoking men, 20.2% but of smoking women only 12.1% had plasma total ascorbate <25 μmol/L Among both smokers and non-smokers, men had lower plasma total ascorbate, α-tocopherol and β-carotene levels and higher dietary intake of saturated fats, serum homocysteine levels and baseline CCA-IMT than women. Among men but not in women, smokers had a greater mean baseline CCA-IMT than non-smokers (p<0.001 for all differences). There were no significant differences between the randomised treatment groups within any stratum.

Atherosclerotic Progression

The average unadjusted increase (slope) of the mean CCA-IMT was 0.020 mm/year among men who were randomised to only placebo, 0.018 mm/year in those who received only vitamin E, 0.017 mm/year in men who received only vitamin C and 0.01 1 mm/year in those who received both vitamins (p=0.043 for heterogeneity). The IMT progression was significantly less in men who were randomised to both vitamins, compared with all other men (p=0.009). The respective means in women were 0.016, 0.015, 0.017 and 0.016 mm/year (not significant).

Of all baseline measurements, serum ferritin and total cholesterol concentrations were most predictive of IMT progression in a step-up linear regression model in men. These and indicator variables for predictive baseline examination months were entered as covariates in linear covariance models predicting IMT progression (Table 5). The covariate-adjusted IMT increase was 50.9% less (0.009 vs. 0.018 mm/year) in men who received both vitamin E and C, compared with other men (p=0.049). Differences between other supplementation groups were not statistically significant. None of treatment effects were significant in women.

In men, the proportion of those who experienced progression was reduced by 74% (95% Cl 36–89%, p=0.003, Table 6) in the group randomised to receive both vitamins, as compared with those who received only placebo. The respective treatment effects were non-significant in groups that received only vitamin E or vitamin C, although there were trends towards protection (Table 5b). These results were unaffected by the choice of covariates. In women, the probability of atherosclerotic progression was similar in all four randomised groups.

In smoking men, the preventive effect of vitamin E on atherosclerotic progression was larger than in non-smoking men (Table 9). In men who received only vitamin E there was 790% (95% Cl 6–95%, p=0.04) less atherosclerotic progression and in those who received both vitamins, 93% (95% Cl 63–99%, p=0.002) less atherosclerotic progression than in men who received only placebo. In smoking men, there was a nonsignificant trend towards protection also among men who were randomised to only vitamin C. There were no statistically significant effects on the probability of atherosclerotic progression in either non-smoking men, smoking women or non-smoking women. Again, entering any additional covariates or deleting any of the entered covariates did not change these results qualitatively and had only very minor effect on the estimates of odds ratio.

Discussion

The present findings are the first demonstration in healthy persons of an atherosclerotic disease preventing effect of supplementation with antioxidative vitamins. Our study suggests that the benefit may be limited to men, and possibly to men who are at increased oxidative stress such as smokers or those who have insufficient status of dietary or endogenous antioxidants. The observed effect modification by gender and smoking status needs to be retested in further clincal trials.

As smoking men had considerably lower baseline levels of both plasma α-tocopherol and ascorbate, it is possible that the confinement of the observed benefit in this group could be simply due to the greater increase of these vitamins due to supplementation. The progression rate in smoking men who received vitamin E and C supplements was lower than in non-smoking men receiving placebo. Thus, in this study the preventive effect of the supplementation was at least equal to the atherosclerosis promoting effect of smoking. This is not a trivial effect from the public health point of view. On the basis of these findings, reasonable doses of C) vitamins E and C jointly can be recommended for regularly smoking men with at least mild hypercholesterolemia. Recommendations concerning other kinds of persons can not be made on the basis of our current findings.

Both the vitamin E and C supplements were safe. There were neither excess deaths nor excess other adverse events in the groups randomised to supplements, although the sample size was not designed to detect effects on either deaths or other disease events. Both the adherence to treatment and the bioavailability of the supplements were good, judged based on increases of plasma vitamin levels. The drop-out rate during the trial was exceptionally low. The observed atherosclerotic progression in the placebo group was of the expected magnitude, suggesting that a potential "healthy participant effect" was small if any. However, the baseline vitamin E and C levels were higher than expected, especially vitamin C in women. This attenuated the achieved percentage increase in plasma vitamin levels and could be a partial explanation for the lack of effect on atherosclerotic progression in women. An alternative explanation is that women in general do not benefit from vitamin E or C supplements, as they have more effective endogenous antioxidative defence systems and in most Western cultures, more diversified diet than men.

This double-blind randomised clinical trial shows that a combined supplementation with reasonable doses of both vitamin E and vitamin C for at least three years can retard the progression of common carotid atherosclerosis substantially in regularly smoking men with at least mild hypercholesterolemia. This preventive effect may be generalizeable to all men. As common carotid plaques and increased intima-media thickness have been shown to predict coronary events (26) this observation may imply benefits with regard to other atherosclerosis-related events

TABLE 5

The causes for drop-outs in the four treatment groups for men and women

| | Men | | | | Women | | | |
|---|---|---|---|---|---|---|---|---|
| Cause for drop-out | Placebo | Vitamin E | Vitamin C | Both vitamins | Placebo | Vitamin E | Vitamin C | Both vitamins |
| Death | 1 | 3 | 1 | 1 | 0 | 0 | 0 | 0 |
| Severe adverse event | 2 | 1 | 1 | 0 | 1 | 2 | 1 | 5 |
| Adverse event | 4 | 1 | 2 | 2 | 1 | 3 | 2 | 0 |
| Refusal or other reason | 5 | 3 | 1 | 1 | 6 | 3 | 3 | 6 |
| Total | 12 | 8 | 5 | 4 | 8 | 8 | 6 | 11 |

TABLE 6

Distributions of the main baseline characteristics of participants in the four randomization strata.

| Baseline characteristic | Smoking men (n = 100) | | | Non-smoking men (n = 125) | | | Smoking women (n = 110) | | | Non-smoking women (n = 123) | | |
|---|---|---|---|---|---|---|---|---|---|---|---|---|
| | Mean | Min. | Max | Mean | Min | Max | Mean | Min. | Max. | Mean | Min. | Max. |
| Age (years) | 59.5 | 46.0 | 70.0 | 60.4 | 45.4 | 70.0 | 58.1 | 47.1 | 69.6 | 60.9 | 46.8 | 70.4 |
| Serum cholesterol (mmol/L) | 6.05 | 3.41 | 8.32 | 6.53 | 4.39 | 9.92 | 6.22 | 4.42 | 8.86 | 4.42 | 11.57 | |
| LDL cholesterol (mmol/L) | 4.33 | 1.42 | 6.36 | 4.73 | 2.45 | 8.14 | 4.25 | 2.57 | 6.91 | 4.67 | 2.03 | 9.05 |
| HDL cholesterol (mmol/L) | 1.12 | 0.55 | 1.83 | 1.14 | 0.68 | 2.21 | 1.35 | 0.69 | 2.75 | 1.43 | 0.68 | 2.55 |
| Serum triglycerides (mmol/L) | 1.55 | 0.38 | 4.40 | 1.73 | 0.51 | 7.51 | 1.47 | 0.54 | 4.59 | 1.63 | 0.45 | 21.60 |
| Plasma fibrinogen (g/L) | 3.79 | 2.1 | 5.5 | 3.47 | 2.1 | 5.4 | 3.83 | 2.4 | 5.6 | 3.59 | 2.2 | 5.4 |
| Plasma total ascobate ($\mu$mol/L) | 57.4 | 5.3 | 138.5 | 68.1 | 12.3 | 131.8 | 69.8 | 11.2 | 138.1 | 82.5 | 21.2 | 127.9 |
| Plasma $\alpha$-tocopherol ($\mu$mol l/L) | 29.7 | 14.7 | 48.0 | 33.5 | 19.4 | 60.7 | 31.2 | 19.2 | 52.8 | 35.4 | 19.9 | 54.3 |
| Plasma $\beta$-carotene (mmol/L) | 0.28 | 0.02 | 0.95 | 0.39 | 0.02 | 2.47 | 0.44 | 0.08 | 1.97 | 0.59 | 0.03 | 2.03 |
| Serum ferritin (mg/L) | 120.0 | 12 | 376 | 142.3 | 9 | 1235 | 88.7 | 8 | 1090 | 66.7 | 5 | 414 |
| Cigarettes/day | 17.3 | 0 | 60 | 0.2 | 0 | 4 | 12.9 | 0 | 28 | 0.1 | 0 | 4 |
| Intake of saturated fat (% of energy) | 17.2 | 9.2 | 29.0 | 15.0 | 7.1 | 27.0 | 16.9 | 9.0 | 28.2 | 14.3 | 6.9 | 22.7 |
| Dietary vitamin E (mg/1000 kcal/d) | 5.0 | 2.2 | 11.3 | 5.3 | 2.5 | 12.4 | 5.1 | 2.2 | 9.1 | 5.5 | 2.8 | 9.3 |
| Dietary vitamin C (mg/1000 kcal/d) | 42.6 | 3.3 | 211 | 49.5 | 6.1 | 191 | 56.5 | 13.5 | 322 | 75.1 | 8.7 | 325 |
| Alcohol intake (g/wk) | 111 | 0 | 491 | 77 | 0 | 440 | 39 | 0 | 225 | 15 | 0 | 161 |
| Total physical activity (min/wk) | 193 | 15 | 600 | 215 | 20 | 655 | 205 | 30 | 640 | 232 | 20 | 905 |
| Weight (kg) | 77.2 | 51.4 | 103.1 | 79.6 | 53.2 | 96.3 | 66.6 | 45.4 | 90.0 | 66.8 | 46.5 | 91.9 |
| Waist-to-hip circumference ratio | 0.95 | 0.81 | 1.04 | 0.95 | 0.80 | 1.03 | 0.84 | 0.69 | 0.97 | 0.81 | 0.72 | 0.95 |
| Systolic blood pressure (mmHg) | 132.3 | 97.7 | 188.3 | 131.2 | 97.3 | 171.7 | 130.3 | 97.0 | 190.0 | 130.1 | 93.3 | 184.7 |
| Diastolic blood pressure (mmHg) | 78.8 | 55.7 | 99.3 | 81.4 | 60.7 | 99.3 | 76.2 | 51.3 | 99.3 | 78.5 | 58.7 | 99.3 |
| Mean CCA-IMT (mm) | 1.10 | 0.62 | 2.04 | 1.04 | 0.55 | 2.53 | 0.92 | 0.60 | 2.23 | 0.92 | 0.59 | 1.49 |

TABLE 7

The mean adjusted 3-year change* of the mean carotid artery intima-media thickness in participants who received vitamin E and C supplements in a multivariate general linear model.

| | Men (n = 225) | | | | | Women (n = 233) | | | | |
|---|---|---|---|---|---|---|---|---|---|---|
| | Yes | | No | | | Yes | | No | | |
| Supplement | Mean (n) | SE | Mean (n) | SE | P | Mean (n) | SE | Mean (n) | SE | P |
| Vitamin E (n = 115) | 0.0118 (56) | 0.0050 | 0.0143 (169) | 0.0022 | 0.571 | 0.0165 (59) | 0.0046 | 0.0170 (174) | 0.0021 | 0.904 |
| Vitamin C (n = 120) | 0.0119 (59) | 0.0050 | 0.0142 (166) | 0.0022 | 0.600 | 0.0174 (61) | 0.0046 | 0.0160 (172) | 0.0021 | 0.732 |
| Both vitamins (n = 113) | 0.0086 (58) | 0.0050 | 0.0175 (167) | 0.0022 | 0.049 | 0.0170 (55) | 0.0047 | 0.0164 (178) | 0.0020 | 0.895 |

Cl denotes confidence interval.
*Change estimated as the linear slope over 6-monthly assessments of mean IMT (mm/year).
†Statistical significance of contrasts to the double-placebo group.
Covariates in the model for both men and women are serum cholesterol and ferritin concentrations, and three indicator variables for baseline examination months.

TABLE 8

The effect of vitamin E and C supplements on the probability of atherosclerotic progression* in multivariate logistic models.

| | Men (n = 225) | | | Women (n = 233) | | |
|---|---|---|---|---|---|---|
| Supplement | OR | 95% Cl | P | OR | 95% Cl | P |
| Vitamin E (n = 115) | 0.56 | 0.23, 1.36 | 0.200 | 1.05 | 0.48, 2.32 | 0.903 |
| Vitamin C (n = 120) | 0.44 | 0.19, 1.06 | 0.066 | 1.08 | 0.49, 2.36 | 0.857 |
| Both vitamins (n = 113) | 0.26 | 0.11, 0.64 | 0.003 | 1.36 | 0.60, 3.04 | 0.461 |

*The slope of the mean IMT dichotomized at median (0.82 mm/year) for men. OR: denotes odds ratio and Cl confidence interval.
Three indicator variables for the three supplementation groups (double placebo as the reference group, n = 106) were entered with age, serum cholesterol and ferritin concentrations, systolic blood pressure, and 11 indicator variables for baseline examination months.

TABLE 9

The effect of vitamin E and C supplements on the probability of atherosclerotic progression in multivariate logistic models.

| | Smoking men (n = 100) | | | Non-smoking men (n = 125) | | | Smoking women (n = 110) | | | Non-smoking women (n = 123) | | |
|---|---|---|---|---|---|---|---|---|---|---|---|---|
| Supplement | OR | 95% Cl | P | OR | 95% Cl | P | OR | 95% Cl | P | OR | 95% Cl | P |
| Vitamin E (n = 115) | 0.21 | 0.05, 0.94 | 0.041 | 1.07 | 0.31, 3.72 | 0.918 | 0.76 | 0.22, 2.62 | 0.666 | 1.13 | 0.36, 3.59 | 0.828 |
| Vitamin C (n = 120) | 0.45 | 0.11, 1.82 | 0.260 | 0.30 | 0.08, 1.08 | 0.065 | 0.69 | 0.19, 2.53 | 0.574 | 0.99 | 0.32, 3.08 | 0.991 |
| Both vitamins (n = 113) | 0.07 | 0.01, 0.37 | 0.002 | 0.55 | 0.17, 1.81 | 0.325 | 1.48 | 0.42, 5.13 | 0.540 | 1.18 | 0.34, 4.09 | 0.794 |

*Three indicator variables for the three supplementation groups (double placebo as the reference group, n = 110) were entered with age, serum cholesterol and ferritin concentrations, systolic blood pressure, and 11 indicator variables for baseline examination months. OR denotes odds ratio and Cl confidence interval.

References

1 Chance B, Sies H, Boveris A. Hydroperoxide metabolism in mammalian organs. *Physiology Review* 1979; 59:527–605.

2 Halliwell B. Free radicals, antioxidants, and human disease: curiosity, cause or consequence. *Lancet* 1994; 344:721–724.

3a Esterbauer H. Striegl G, Puhl H, Rotheneder M. Continuous monitoring of In vitro oxidation of human low density lipoprotein. *Free Radical Research Communications* 1989; 6:67–75.

3b Esterbauer H, Gebicki J, Puhl H. Günther J. The role of lipid peroxidation and antioxidants in oxidative modification of LDL. *Free Radials in Biology and Medicine* 1992; 13, 341–390.

4 Steinberg D, Parthasarathy S, Carew T E, Khoo J C, Witztum J L. Beyond cholesterol. Modifications of low-lipoprotein that increase its atherogenecity. *N Engl J Med* 20 1989; 320(14):915–924.

5 Hennekens C H, Gaziano J M, Manson J E, Buring J E. The antioxidant vitamin-cardiovascular disease hypothesis is still promising, but remains unproved: the need for randomised trials. *Am J Clin Nutr* 1995; 62,1377S–1380S.

6 Levine M, Dhariwal K R, Welch R W, Wang Y, Park J B. Determination of optimal vitamin C requirements in humans. *Am. J. Clin. Nutr.* 1995, 62, 1347S–1356S.

7 Burton G W, Traber M G. Vitamin E: antioxidant activity, biokinetics, and bioavailability. *Annu. Rev. Nutr.* 1990, 10, 357–382.

8 Kagan V E, Serbinova E A, Forte T, Scita G, Packer L. Recycling of vitamin E in human low density lipoproteins. *J. Lipid Res.* 1992, 33, 385–397.

9 Niki E, Noguchi N, Tsuchihashi H, Gotoh N. Interaction among vitamin C, vitamin E, and betacarotene. *Am. J. Clin. Nutr.* 1995,I,1322s-1326s.

10 D. Horring, *S. Afr. Med. J.* 1981,60, 818–823.

11 Washko P W, Welch R W, Dhariwal K R, Wang Y, Levine M. Ascorbic acid and dehydroascorbic acid analyses in biological samples. *Anal. Biochem.* 1992, 204,1–14.

12 Heinonen O P, Albanes D. The effect of vitamin E and beta carotene on the incidence of lung cancer and other cancers in male smokers. *N. Engl. J. Med.* 1994, 330, 1029–1035.

13 Nyyssonen K, Poulsen H E, Hayn M, Agerbo P, Porkkala-Sarataho E, Kaikkonen J et al. Effect of supplementation of smoking men with plain or slow release ascorbic acid on lipoprotein oxidation. *European Journal of Clinical Nutrition* 1997, 51(3), 154–163.

14a Nyyssönen, K; Porkkala, E; Salonen, R; Korpela, H; and Salonen, J. T; Increase in oxidation resistance of atherogenic serum lipoproteins following antioxidant supplementation: a randomized double-blind placebo-controlled clinical trial. *European Journal of Clinical Nutrition*, 1994, 48, pages 633–642

14b Porkkala-Sarataho E, Nyyssönen K, Kaikkonen J, Poulsen H E, Hayn M, Salonen R, et al. A randomized, single-blinded, placebo-controlled trial of reasonable dose of alpha-tocopherol in oxidation resistance of atherogenic lipoproteins and vitamin E absorption. *Am J Clin Nutr* 1998; 68: 1034–41.

15 Salonen et al.,*Am. J. Nutr.*, A randomised, single blind, placebo-controlled trial of the effects of 200 mg α-tocopherol on the oxidation resistance of artherogenic lipoproteins, 1998;68, 1034–41.

16 Bhagavan H N et al., Correlation Between the Disintegration Time and the Bioavailability of Vitamin C-tablets, *Pharmaceutical Research*, 1993, 10(2).pages 239–242

17 H.Gjelstrup Kristensen, N. Møller, Almen Farmaci I, *Dansk Farmaceutforenings forlag*, 1980: p.93–97.

18 Salonen J T, Ylä-Herttuala S, Yamamoto R, Butler S, Korpela H, Salonen R, et al. Autoantibody against oxidised LDL and progression of carotid atherosclerosis. *Lancet* 1992; 339: 883–7.

19 Salonen J T, Nyyssönen K, Salonen R, Porkkala-Sarataho E, Tuomainen T-P, Dicfalusy U, et al. Lipoprotein oxidation and progression of carotid atherosclerosis. *Circulation* 1997; 95: 8405.

20 Witztum J L. The oxidation hypothesis of atherosclerosis. *Lancet* 1994; 344: 793–5.

21 Steinberg D. Clinical trials of antioxidants in atherosclerosis: are we doing the right thing? *Lancet* 1995; 346: 36–8.

22 Diplock A T. Will the 'good fairies' please prove to us that vitamin E lessens human degenerative disease? *Free Radic Res* 1997; 27: 511–32.

23 Diaz M N, Frei B, Vita J A, Keaney J F Jr. Antioxidants and atherosclerotic heart disease. *N Engl J Med* 1997; 337: 408–16.

24 Salonen J T. Epidemiological studies on antioxidants, lipid peroxidation and atherosclerosis. *Arch Toxicol Suppl.* 1998; 20: 249–67.

25 Riemersma R A, Wood D A, Macintyre C C, Elton R A, Gey K F, Oliver M F. Risk of angina pectoris and plasma concentrations of vitamins A, C, and E and carotene. *Lancet* 1991; 337: 1–5

26 Blot W J, Li J-Y, Taylor P R et al. Nutrition intervention trials in Linxian, China: Supplementation with specific vitamin/mineral combinations, cancer incidence, and disease-specific mortality in the general population. *J Natl Cancer Inst* 1993; 85: 1483–92.

27 Rapola J M, Virtamo J, Haukka J K, Heinonen O P, Albanes D, Taylor P R, et al. Effect of vitamin E and beta carotene on the incidence of angina pectoris. A randomized, double-blind, controlled trial. *JAMA* 1996; 275: 693–8.

28 Stephens N G, Parsons A, Schofield P M, et al. Randomised controlled trial of vitamin E in patients with coronary disease: Cambridge Heart Antioxidant Study (CHAOS). *Lancet* 1996; 347: 781–86.

29 Mitchinson M J, Stephens N G, Parsons A, Bligh E, Schofield P M, Brown M J. Mortality in the CHAOS trial. *Lancet* 1999; 353: 381–2.

30 Salonen R, Nyyssönen K, Porkkala E, Rummukainen J, Belder R, Park J-S, et al. Kuopio Atherosclerosis Prevention Study (KAPS): A population-based primary preventive trial of the effect of LDL lowering on atherosclerotic progression in carotid and femoral arteries. *Circulation* 1995; 92: 1758–64.

31 Rimm E B, Stampfer M J, Ascherio A, Giovannucci E, Colditz G A, Willet W C. Vitamin E consumption and the risk of coronary heart disease in men. *N Engl J Med* 1993; 328: 1450–56.

32 Kushi L H, Folsom A R, Prineas R J, Mink P J, Wu Y, Bostick R M. Dietary antioxidant vitamins and death from coronary heart disease in postmenopausal women. *N Engl J Med* 1996; 334: 1156–62.

33 Steinberg D. Clinical trials of antioxidants in atherosclerosis: are we doing the right thing? *Lancet* 1995; 346: 363–8.

34 Tribble D L. AHA Science Advisory. Antioxidant consumption and risk of coronary heart disease: emphasis on vitamin C, vitamin E, and beta-carotene: A statement for healthcare professionals from the American Heart Association. *Circulation* 1999; 99: 591–5.

35 Frei B, England L, Ames B N. Ascorbate is an outstanding antioxidant in human blood plasma. *Proc Natl Acad Sci* 1989; 86: 6377–81.

36 Azzi A, Aratri E, Boscoboinik D, Clement S, Ozer N K, Ricciarelli R, et al. Molecular basis of alpha-tocopherol control of smooth muscle cell proliferation. *Biofactors* 1998; 7: 3–14.

37 Packer J E, Slater T F, Wilson R L. Direct observation of a free radical interaction between vitamin E and vitamin C. *Nature* 1979; 278: 737–8.

38 Neutzil J, Thomas S R, Stocker R. Requirement for, promotion, or inhibition by alpha-tocopherol of radical-induced initiation of plasma lipoprotein lipid peroxidation. *Free Red Biol Med* 1997; 22: 57–71.

39 Nyyssönen K, Parviainen M T, Salonen R, Tuomilehto J, Salonen J T. Vitamin C deficiency and risk of myocardial infarction: prospective population study of men from eastern Finland. *Brit Med J* 1997; 314: 634–8.

40 Salonen J T, Salonen R. Ultrasound B-mode imaging in observational studies of atherosclerotic progression. *Circulation* 1993; 87 (suppl. II): 55–65.

41 Salonen J T, Korpela H, Salonen R, Nyyssönen K. Precision and reproducibility of ultrasonographic measurements of progression of common carotid artery atherosclerosis. *Lancet* 1993; 341: 1158–9.

42 Selzer R H, Hodis H N, Kwong-Fu H, Mack W J, Lee P L, Liu C R, et al. Evaluation of computerized edge tracking for quantifying intima-media thickness of the common carotid artery from B-mode ultrasound images. *Atherosclerosis* 1994; 111: 1–11.

43 Lakka T A, Venäläinen J M, Rauramaa R, Salonen R, Tuomilehto J, Salonen J T. Relation of leisure-time physical activity and cardiorespiratory fitness to the risk of acute myocardial infarction in men. *N Engl J Med* 1994; 330: 1549–54.

44 Voutilainen S, Alfthan G, Nyyssönen K, Salonen R, Salonen J T. Association between elevated plasma total homocysteine and increased common carotid artery wall thickness. *Ann Med* 1998; 30: 300–6.

What is claimed is:

1. A delivery system for oral delivery of the antioxidants vitamin C and vitamin E to obtain high concentrations thereof and a controlled ratio between vitamin C and vitamin E in blood plasma in humans or animals, characterized in that it has a slow release of vitamin C and a plain release of vitamin E;

wherein vitamin C is present in an amount in the delivery system so as to deliver a daily dose corresponding to 60 mg–2 g of vitamin C, and vitamin E is present in an amount in the delivery system so as to deliver a daily dose corresponding to 50 mg–500 mg of α-tocopherol, and the antioxidants are present in amounts so as to obtain vitamin C and vitamin E in a ratio in the blood plasma of 1:1 to 3:1;

wherein the solubility of vitamin E is such that at least 90% of vitamin E is dissolved in less than 30 minutes under the conditions of Test B; and wherein the solubility of vitamin C is such that less than 40% of vitamin C is dissolved after 1 hour under the conditions of Test A; and wherein said delivery system achieves a concentration of vitamin E in the blood plasma of at least 20 μmol/liter and a concentration of vitamin C in the blood plasma of at least 40 μmol/liter.

2. A delivery system according to claim 1, characterized in that it is a system comprising a tablet comprising at least two non-identical delivery principles, wherein a) one delivery principle comprises
   i) vitamin C;
   ii) a pharmaceutically acceptable excipient for controlling the slow release of vitamin C; and
   iii) other pharmaceutically acceptable excipients; and
b) another delivery principle comprises
   i) vitamin E; and
   ii) pharmaceutically acceptable excipients.

3. A delivery system according to claim 1, characterized in that vitamin C is ascorbic acid and vitamin E is selected from d-α-tocopheryl acetate, d-α-tocopheryl acid succinate, d-α-tocopherol, d-β-tocopherol, d-γ-tocopherol, d-δ-tocopherol, d-α-tocotrienol, d-β-tocotrienol, d-γ-tocotrienol, d-δ-tocotrienol, dl-α-tocopherol, dl-α-tocopheryl acetate, dl-α-tocopheryl calcium succinate, dl-α-tocopheryl nicotinate, dl-α-tocopheryl linoleate/oleate, and derivatives or stereo isomeric forms of the above compounds.

4. A delivery system according to claim 1, wherein the daily dose of vitamin C corresponds to 100 mg–1.5 g of ascorbic acid.

5. A delivery system according to claim 1, wherein the daily dose of vitamin E corresponds to 100 mg–250 mg of α-tocopherol.

6. A delivery system according to claim 1, wherein the daily dose of vitamin C and E is delivered by 1 to 8 dosage units.

7. A delivery system according to claim 1, wherein the daily dose of vitamin C and E is delivered by 1 or 2 dosage units.

8. A method of treating oxidative stress disorders, said method comprising administering to an individual a combination of vitamin C and vitamin E in sufficient amounts to raise the concentration of said vitamins in blood plasma to a ratio of approximately 1:1 to 3:1, in not more than 8 weeks from the first administration, wherein vitamin C is released by a slow release formulation and vitamin E is released by a plain release formulation; and wherein the concentration of vitamin E in the blood plasma is at least 20 μmol/liter and the concentration of vitamin C in the blood plasma is at least 40 μmol/liter; and wherein the administering is in amounts corresponding to a daily dose of 60 mg–2 g of vitamin C and corresponding to a daily dose of 50 mg–500 mg of α-tocopherol.

9. A method according to claim 8, wherein the raising is with 4 weeks.

10. A method according to claim 8, wherein the method achieves, in blood plasma, a concentration of vitamin C of from about 102 to 142 μmol/liter, and a concentration of vitamin E of from about 46 to 65 μmol/liter.

11. A method of treating oxidative stress disorders, said method comprising daily administering to an individual at least one dosage unit comprising a combination of vitamin C and vitamin E in sufficient amounts to raise the concentration of said vitamins in blood plasma to a controlled ratio;

wherein said vitamin C is formulated in a slow-release preparation and vitamin E is formulated only in plain-release formulation;

wherein the concentration of vitamin E in the blood plasma is at least 20 µmol/liter, and the concentration of vitamin C in the blood plasma is at least 40 µmol/liter;

wherein the antioxidants are present in amounts so as to obtain vitamin C and vitamin E in a in the blood plasma of 1:1 to 3:1;

wherein the at least one dosage units delivers a daily dose corresponding to 60 mg–2 g of vitamin C and a daily dose corresponding to 50 mg–500 mg of α-tocopherol; and wherein the formulation of vitamin E is such that at least 90% of vitamin E is dissolved in less than 30 minutes under the conditions of Test B, and the formulation of vitamin C is such that less than 40% of vitamin C is dissolved after 1 hour under the conditions of Test A.

12. A method according to claim 11, wherein the method achieves, in blood plasma, a concentration of vitamins C of from about 102 to 142 µmol/liter, and a concentration of vitamin E of from about 46 to 65 µmol/liter.

13. A method according to claim 11, wherein the at least one dosage unit is at most 8 dosage units.

14. A method according to claim 13, wherein the at least one dosage unit is 1 or 2 dosage units.

15. A delivery system according to claim 1, substantially free of histidine.

* * * * *

UNITED STATES PATENT AND TRADEMARK OFFICE
CERTIFICATE OF CORRECTION

PATENT NO. : 6,805,880 B1
DATED : October 19, 2004
INVENTOR(S) : Bent Hojgaard et al.

It is certified that error appears in the above-identified patent and that said Letters Patent is hereby corrected as shown below:

Column 29,
Line 5, "a in" should read -- a ratio in --.

Column 30,
Line 4, "vitamins" should read -- vitamin --.

Signed and Sealed this

Fifteenth Day of February, 2005

JON W. DUDAS
*Director of the United States Patent and Trademark Office*